US010413652B2

(12) United States Patent
Foley et al.

(10) Patent No.: US 10,413,652 B2
(45) Date of Patent: Sep. 17, 2019

(54) SYSTEMS AND METHODS FOR USE AND CONTROL OF AN AUTOMATED SEPARATOR WITH ADSORPTION COLUMNS

(75) Inventors: John T. Foley, Wheeling, IL (US); Jonathan Prendergast, Palatine, IL (US); Lan T. Nguyen, Vernon Hills, IL (US); Brian C. Case, Lake Villa, IL (US)

(73) Assignee: FENWAL, INC., Lake Zurich, IL (US)

( * ) Notice: Subject to any disclaimer, the term of this patent is extended or adjusted under 35 U.S.C. 154(b) by 987 days.

(21) Appl. No.: 14/110,587

(22) PCT Filed: Apr. 13, 2011

(86) PCT No.: PCT/US2011/032320
§ 371 (c)(1),
(2), (4) Date: Oct. 21, 2013

(87) PCT Pub. No.: WO2012/141697
PCT Pub. Date: Oct. 18, 2012

(65) Prior Publication Data
US 2014/0291248 A1    Oct. 2, 2014

(51) Int. Cl.
*A61M 1/36*    (2006.01)

(52) U.S. Cl.
CPC .......... *A61M 1/362* (2014.02); *A61M 1/3639* (2013.01); *A61M 1/3663* (2013.01);
(Continued)

(58) Field of Classification Search
CPC .............. A61M 1/0218; A61M 1/0222; A61M 1/0227; A61M 1/13679;
(Continued)

(56) References Cited

U.S. PATENT DOCUMENTS

| 4,215,688 A * | 8/1980 | Terman | A61M 1/3679 604/6.04 |
| 4,374,731 A * | 2/1983 | Brown | A61M 1/3496 210/321.65 |

(Continued)

FOREIGN PATENT DOCUMENTS

| EP | 0 112 094 A1 | 6/1984 |
| EP | 1283064 A2 | 2/2003 |

(Continued)

OTHER PUBLICATIONS

Robert A. Koll, Ig-Therasorb Immunoadsorption for Selective Removal of Human Immunoglobins in Diseases Associated with Pathogenic Antibodies of All Classes and IgG Subclasses, Immune Complexes, and Fragments of Immunoglobins, 2 Therapeutric Apheresis 147, 147-152 (1998).*

(Continued)

*Primary Examiner* — Krishnan S Menon
*Assistant Examiner* — Brad Gordon
(74) *Attorney, Agent, or Firm* — Cook Alex Ltd.

(57) ABSTRACT

Blood treatment systems and methods are provided for combining a blood separation system and an adsorption device. The blood separation system is configured to separate a blood component from blood, while the adsorption device is configured to receive at least a portion of the separated blood component and process it. The blood separation system includes a fluid flow element and a controller. The fluid flow element is configured for flowing the separated blood component into the adsorption device. The controller controls the fluid flow element based at least in part on one or more processing parameters. The processing parameters include a maximum flow rate of the separated blood component flowed into the adsorption device, a maximum pressure of the separated blood component flowed into the adsorption device, and/or the volume of fluid in a location of the system.

12 Claims, 14 Drawing Sheets

(52) U.S. Cl.
CPC ........ *A61M 1/3679* (2013.01); *A61M 1/3693* (2013.01); *A61M 1/3696* (2014.02)

(58) Field of Classification Search
CPC .... A61M 1/0209–0236; A61M 1/3639; A61M 1/3641; A61M 1/3469; A61M 1/3663
See application file for complete search history.

(56) References Cited

U.S. PATENT DOCUMENTS

| | | | | |
|---|---|---|---|---|
| 4,824,145 | A * | 4/1989 | Carlsson | A61M 39/10 285/38 |
| 4,994,188 | A * | 2/1991 | Prince | A61M 1/34 210/321.68 |
| 5,194,145 | A | 3/1993 | Schoendorfer | |
| 5,277,701 | A | 1/1994 | Christie et al. | |
| 5,316,667 | A | 5/1994 | Brown et al. | |
| 5,632,893 | A | 5/1997 | Brown et al. | |
| 5,672,481 | A * | 9/1997 | Minshall | A61M 1/0281 422/44 |
| 5,868,696 | A * | 2/1999 | Giesler | F04B 43/1253 494/62 |
| 5,958,250 | A * | 9/1999 | Brown | A61M 1/3693 210/745 |
| 6,294,090 | B1 | 9/2001 | Nussbaumer et al. | |
| 6,312,607 | B1 | 11/2001 | Brown et al. | |
| 6,569,112 | B2 | 5/2003 | Strahilevitz | |
| 6,582,386 | B2 | 6/2003 | Min et al. | |
| 6,979,309 | B2 | 12/2005 | Burbank et al. | |
| 7,267,658 | B2 | 9/2007 | Treu et al. | |
| 7,462,161 | B2 | 12/2008 | O'Mahony et al. | |
| 2003/0146154 | A1 * | 8/2003 | Moriarty | A61M 1/16 210/646 |
| 2004/0019313 | A1 * | 1/2004 | Childers | A61M 1/1696 604/5.01 |
| 2004/0082459 | A1 * | 4/2004 | Min | A61M 1/3693 494/37 |
| 2005/0048644 | A1 | 3/2005 | Hedrick | |
| 2009/0149795 | A1 * | 6/2009 | O'Mahony | A61M 1/34 604/4.01 |
| 2009/0215602 | A1 * | 8/2009 | Min | A61M 1/3693 494/4 |
| 2009/0221948 | A1 | 9/2009 | Szamosfalvi et al. | |
| 2010/0042037 | A1 * | 2/2010 | Felt | A61M 1/36 604/6.04 |
| 2010/0158893 | A1 | 4/2010 | Sawada | |
| 2011/0224645 | A1 * | 9/2011 | Winqvist | A61M 1/3679 604/500 |

FOREIGN PATENT DOCUMENTS

| | | |
|---|---|---|
| WO | WO98/52629 A2 | 11/1998 |
| WO | WO2012/141889 A1 | 10/2012 |

OTHER PUBLICATIONS

Extended European Search Report for European Patent Appl'n. No. 11863485.6, dated Mar. 13, 2015.

Partial Supplementary European Search Report for European Patent Appl'n. No. 11863485.6, dated Nov. 17, 2014.

International Search Report and Written Opinion for PCT Patent Appl'n. No. PCT/US11/32320, dated Jun. 27, 2011.

"Globaffin-First Synthetic Broadband—Immunoadsorber," Fresenius Medical Care, 2006.

"Immunosorba—Protein a Column dor Immunoadsorption," Fresenius Medical Care, 2005.

"Beyond Diet and Drug Therapy . . . Liposorber," Kaneka Medical Products.

* cited by examiner

SYSTEMS AND METHODS FOR USE AND CONTROL OF AN AUTOMATED SEPARATOR WITH ADSORPTION COLUMNS

BACKGROUND

Field of the Disclosure

The disclosure relates to blood treatment systems and methods. More particularly, the disclosure relates to systems and methods for combining an adsorption device and a blood separation system.

Description of Related Art

Various blood processing systems now make it possible to collect particular blood constituents, rather than whole blood, from donors or patients. Typically, in such systems, whole blood is drawn from a donor, the particular blood component or constituent is removed and collected, and the remaining blood constituents are returned to the donor. By thus removing only particular constituents, potentially less time is needed for the donor's body to return to pre-donation levels, and donations can be made at more frequent intervals than when whole blood is collected. This increases the overall supply of blood constituents, such as plasma and platelets, made available for health care.

Whole blood is typically separated into its constituents through centrifugation. This requires that the whole blood be passed through a centrifuge after it is withdrawn from, and before it is returned to, the donor. To avoid contamination and possible infection of the donor, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber in the fluid processing assembly during a blood separation step. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of a separation chamber included as part of the fluid processing assembly. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid processing assembly. For example, one application of therapeutic plasma exchange involves separating plasma from cellular blood components, collecting the plasma, and returning the cellular blood components and a replacement fluid to the donor.

After the blood has been separated into its constituent parts, it may be desirable to further process one more of the separated components. For example, in an alternative version of a therapeutic plasma exchange procedure, rather than replacing a patient's plasma with a different fluid, the patient's own plasma may be treated and returned after separation. This may be most efficiently achieved by pairing the blood separation system with a secondary processing device, such as an adsorption device or column. The adsorption device will remove undesirable substances from the plasma by immuno-adsorption. The exact substances removed depend upon the needs of the patient. For example, the substances removed from the plasma by the adsorption device may include low-density lipoproteins and Lipoprotein (a) for patients suffering from severe hypercholesterolemia. In another example, pathogenic antibodies may be removed from the plasma, for patients suffering from auto-immune diseases and organ transplant rejection, or as a pre-treatment before transplantation. In yet another example, fibrinogen, fibrin, and/or C-reactive protein may be removed from the plasma, for treating microcirculation disorders and ischemic tissue damage. Exemplary adsorption devices include the TheraSorb® line of products from Miltenyi Biotec GmbH Corporation of Bergisch Gladbach, Germany. Other examples of adsorption devices suitable for removing undesirable substances from plasma are described in greater detail in U.S. Pat. No. 6,569,112 to Strahilevitz, which is incorporated herein by reference.

One disadvantage of known systems which combine a blood separation system with an adsorption device is the amount of manual intervention and oversight required. Typically, an operator must monitor the adsorption device to ensure that a suitable amount of plasma is entering the adsorption device, so as to not overload the device. If the operator does not properly monitor the adsorption device, plasma will not be properly processed and may be returned to the patient without having the undesirable substances removed therefrom. Furthermore, when using "active" adsorption columns the operator must actively monitor any reservoir bags to ensure that large amounts of blood components are not removed from the patient without proper component replacement, as decreased effective circulating volume ("ECV") can severely compromise a patient's health. Accordingly, the need remains for blood treatment systems and methods which combine the separation and further processing functions while eliminating or at least reducing the amount of manual intervention and oversight required.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a blood treatment system is provided which includes the combination of a blood separation system and an adsorption device. The blood separation system is configured to separate a blood component from blood, while the adsorption device is configured to receive at least a portion of the separated blood component from the blood separation system and process it. The blood separation system includes a fluid flow element and a controller. The fluid flow element is configured for flowing the separated blood component into the adsorption device. The controller controls the fluid flow element based at least in part on one or more processing parameters, which include a maximum flow rate of the separated blood component flowed into the adsorption device and/or a maximum pressure of the separated blood component flowed into the adsorption device.

In another aspect, a blood treatment system is provided which includes the combination of a blood separation system and an adsorption device. The blood separation system is configured to separate a blood component from blood, while the adsorption device is configured to receive at least a portion of the separated blood component from the blood separation system and process it. Each of the blood separation system and the adsorption device includes a fluid flow element, with the fluid flow element of the blood separation system being configured for flowing the separated blood component to a location and the fluid flow element of the adsorption device being configured for flowing the separated blood component from the location and into the adsorption device. The blood separation system includes a controller which controls the fluid flow element of the blood separation system based at least in part on one or more characteristics of the location.

In yet another aspect, a method is provided for separating a blood component from blood using a blood separation system and an adsorption device. The method includes separating a blood component from blood in a blood separation system. At least a portion of the separated blood component is flowed into an adsorption device at an actual flow rate and an actual pressure. The actual flow rate and/or the actual pressure of the separated blood component flowing into the adsorption device is controlled based, at least in part, on one or more processing parameters, which include a maximum flow rate and/or a maximum pressure. The method further includes processing the separated blood component using the adsorption device.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
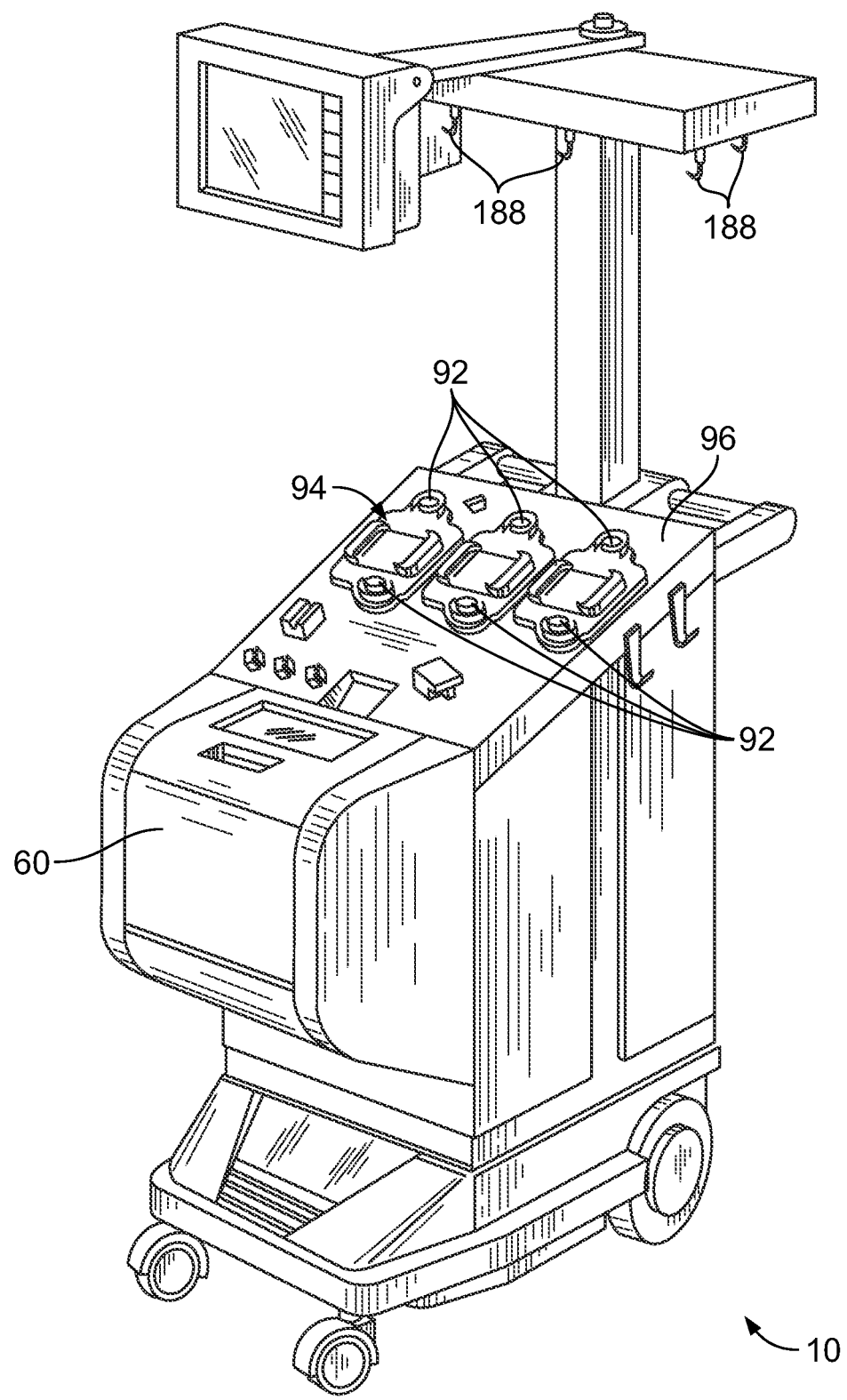
FIG. 1 is a perspective view of an exemplary centrifuge system of a blood separation system that may be used in combination with an adsorption device, in accordance with an aspect of the present disclosure.

Blood treatment systems according to the present disclosure include a blood separation system and an adsorption device. In one embodiment, the blood separation system comprises the combination of a reusable separation device and a single-use tubing set. The separation device may be variously provided without departing from the scope of the present disclosure, but FIG. 1 shows an exemplary durable centrifuge system 10 that may be employed in blood treatment systems according to the present disclosure. The centrifuge system 10 may be provided according to known design, such as the system currently marketed as the AMICUS® separator by Fenwal, Inc. of Lake Zurich, Ill., as described in greater detail in U.S. Pat. No. 5,868,696, which is hereby incorporated herein by reference. The centrifuge system 10 can be used for processing various fluids, but is particularly well suited for processing whole blood and other suspensions of biological cellular materials. While fluid treatment principles will be described herein with reference to one particular system, it should be understood that these principles may be employed with other blood separation devices without departing from the scope of the present disclosure. Further, it should also be appreciated that the blood treatment systems according to the present disclosure are not limited to blood separation by centrifugation, as the principles described herein may also be employed with blood separation devices which separate blood by other means, such as by a "spinning membrane" of the type described in U.S. Pat. No. 5,194,145 to Schoendorfer, which is hereby incorporated herein by reference.

Figure 2:
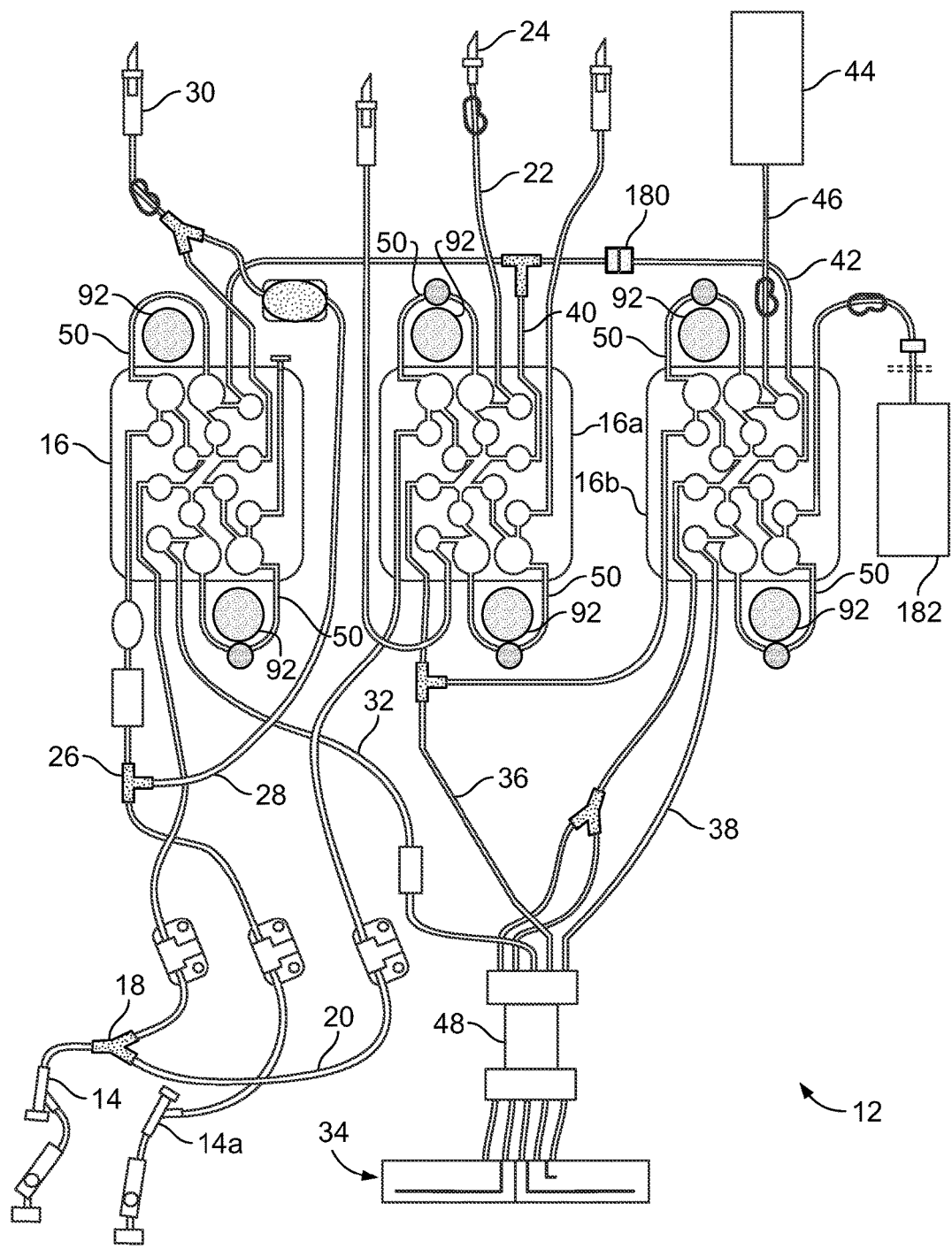
FIG. 2 is a diagrammatic view of an exemplary disposable flow circuit that may be used in combination with the centrifuge system of FIG. 1.

FIG. 2 illustrates a disposable flow circuit 12 that may be used in combination with the centrifuge system 10 of FIG. 1 to provide a blood separation system. The flow circuit 12 includes a variety of tubing and a number of components, only some of which will be described herein in greater detail. It should be understood that FIG. 2 illustrates only one example of a flow circuit which may be used in combination with the centrifuge system 10 of FIG. 1 and differently configured flow circuits may also be employed without departing from the scope of the present disclosure.

The illustrated flow circuit 12 is a "two needle" system, which includes a pair of blood source access devices 14 and 14a (e.g., phlebotomy needles) for fluidly connecting a blood source with the flow circuit 12. The blood source access devices 14 and 14a are connected by tubing to a left cassette 16, which will be described in greater detail herein. One of the blood source access devices 14 is used to draw blood from the blood source into the flow circuit 12 and is connected to the left cassette 16 by a y-connector 18. The other leg of the y-connector 18 is connected to tubing 20 which leads to a middle cassette 16a. The tubing 20 is connected, through the middle cassette 16a, to additional tubing 22, which includes a container access device 24 (e.g., a sharpened cannula or spike connector) for accessing the interior of an anticoagulant container (not illustrated). During a blood treatment operation, anticoagulant from the anticoagulant container is added to the blood from the blood source at the y-connector 18 prior to entering the left cassette 16.

The other blood source access device 14a is used to deliver or return blood, a blood component, and/or some other replacement fluid to the blood source and is also connected to the left cassette 16 by a y-connector 26. The other leg of the y-connector 26 is connected to tubing 28 connected at its other end to a container access device 30. Although not illustrated, the container access device 30 may be associated with a container having an amount of fluid (e.g., saline) to be used to prime the flow circuit 12 and/or delivered to the blood source via the blood source access device 14a.

The left cassette 16 also includes tubing 32 which is connected to a blood separation chamber 34 of the flow circuit 12 for flowing anticoagulated blood thereto. The blood separation chamber 34 separates the blood into its constituent parts (as will be described in greater detail herein) and returns the blood components to the flow circuit 12. In one embodiment, cellular blood components are returned to the middle cassette 16a of the flow circuit 12 from the blood separation chamber 34 via tubing 36, while substantially cell-free plasma is returned to a right cassette 16b of the flow circuit 12 from the blood separation chamber 34 via tubing 38. The cellular blood components may be pumped to the left cassette 16 via tubing 40, where they are returned to the blood source. The plasma may be pumped back to the left cassette 16 via tubing 42 for return to the blood source and/or it may be pumped into a container 44 via different tubing 46. The destination of the plasma (and the other fluids passing through the cassettes) depends upon the actuation of the various valves of the cassettes, as will be described in greater detail herein. The various tubing connected to the blood separation chamber 34 are bundled in an umbilicus 48, which will be described in greater detail herein.

Additional tubing may be connected from one port of a cassette to another port of the same cassette, so as to form tubing loops 50 which interact with a fluid flow element or pump to flow fluid through the flow circuit 12, as will be described in greater detail herein.

A. The Centrifuge

The centrifuge system 10 includes a centrifuge 52 (FIGS. 3 and 4) used to centrifugally separate blood components. The centrifuge system 10 may be programmed to separate blood into a variety of components (e.g., platelet-rich plasma and red cells). For illustrative purposes, a therapeutic plasma exchange procedure, in which the centrifuge 52 separates whole blood into cellular components (e.g., red blood cells and platelets) and substantially cell-free plasma, will be described herein. However, the principles described and claimed herein may be employed with other blood separation procedures without departing from the scope of the present disclosure.

Figure 3:
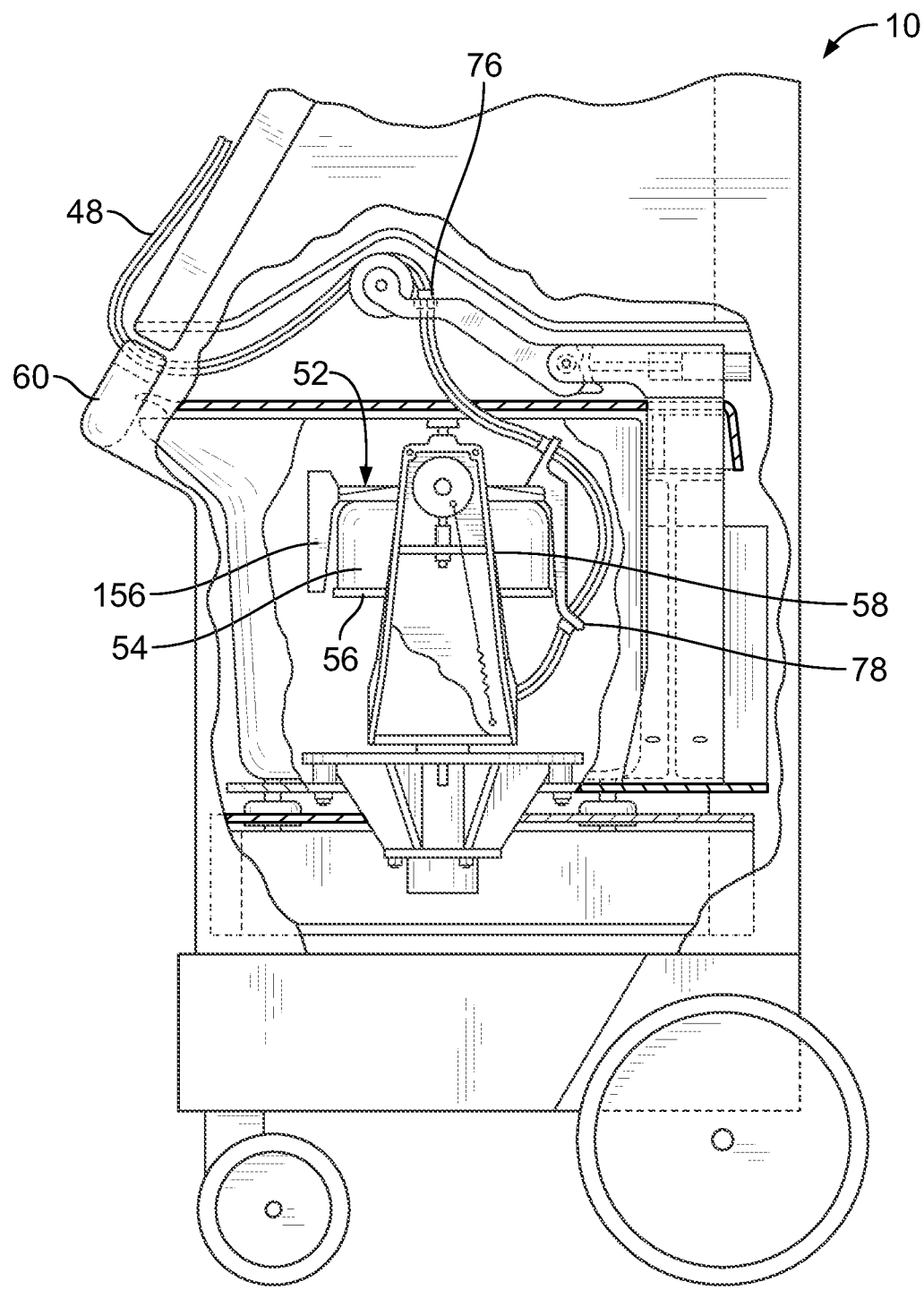
FIG. 3 is a side elevational view, with portions broken away and in section, of the centrifuge system of FIG. 1, with a centrifuge bowl and spool of the system being shown in their operating position.
Figure 4:
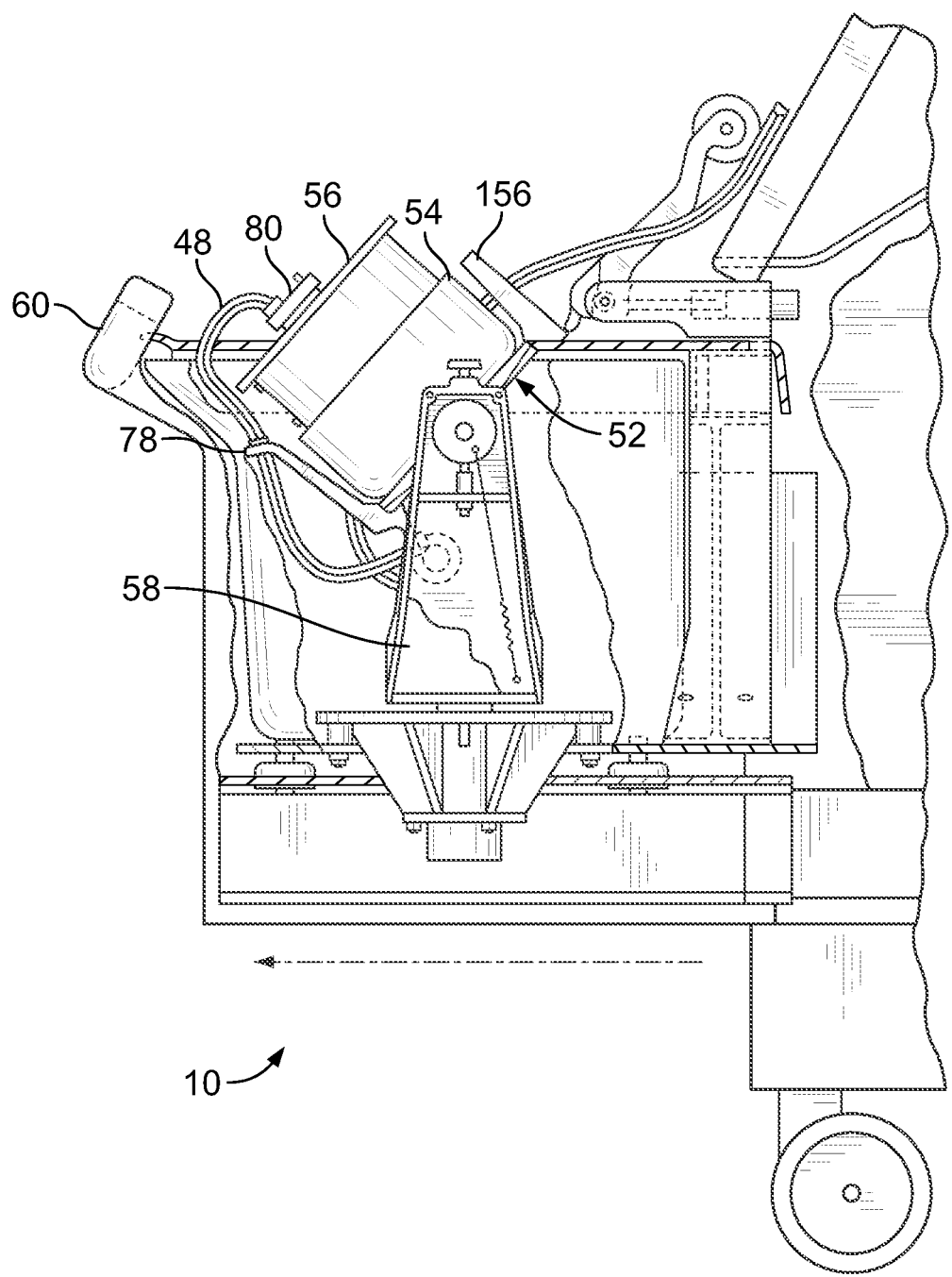
FIG. 4 is a side elevational view, with portions broken away and in section, of the centrifuge system of FIG. 1, with the centrifuge bowl and spool shown in an upright position for receiving a blood separation chamber.

The illustrated centrifuge 52 is of the type shown in U.S. Pat. No. 5,316,667 to Brown et al., which is incorporated herein by reference. The centrifuge 52 comprises a bowl 54 and a spool 56. The bowl 54 and spool 56 are pivoted on a yoke 58 between an operating position (FIG. 3) and a loading/unloading position (FIG. 4). The centrifuge 52 is housed within the interior of the centrifuge system 10, so a door 60 is provided to allow access to the centrifuge 52 for loading and unloading the blood separation chamber 34, as will be described in greater detail herein. The door 60 remains closed during operation to protect and enclose the centrifuge 52.

When in the loading/unloading position, the spool 56 can be opened by movement at least partially out of the bowl 54, as FIG. 4 shows. In this position, the operator wraps the flexible blood separation chamber 34 about the spool 56 (see FIG. 5). Closure of the spool 56 and bowl 54 encloses the chamber 34 for processing. When closed, the spool 56 and bowl 54 are pivoted into the operating position of FIG. 3 for rotation about an axis.

B. The Blood Separation Chamber

Figure 6:
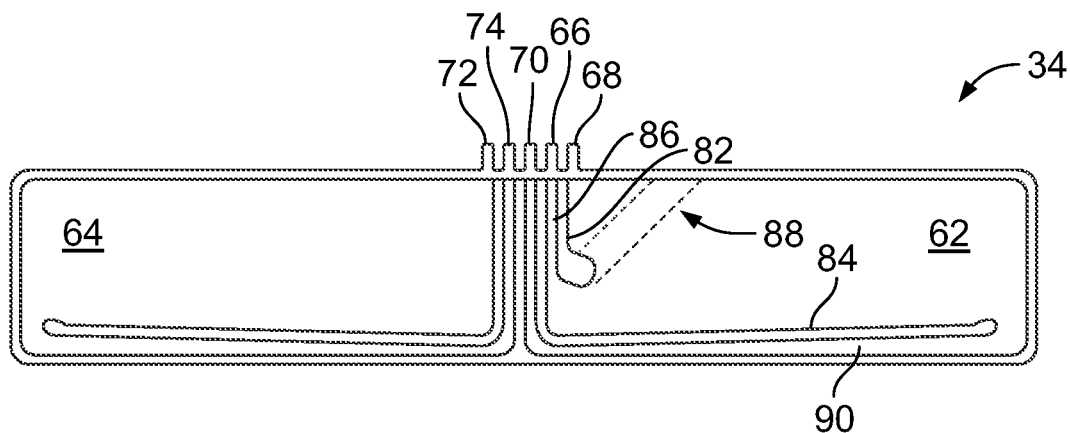
FIG. 6 is a plan view of the blood separation chamber of FIG. 5, out of association with the spool.

FIG. 6 shows a representative embodiment of a blood separation chamber 34 which may be used in connection with the present disclosure. The chamber 34 shown in FIG. 6 allows for either single- or multi-stage processing. When used for multi-stage processing, a first stage 62 separates whole blood into first and second components. Depending on the nature of the separation procedure, one of the components may be transferred into a second stage 64 for further processing.

Figure 5:
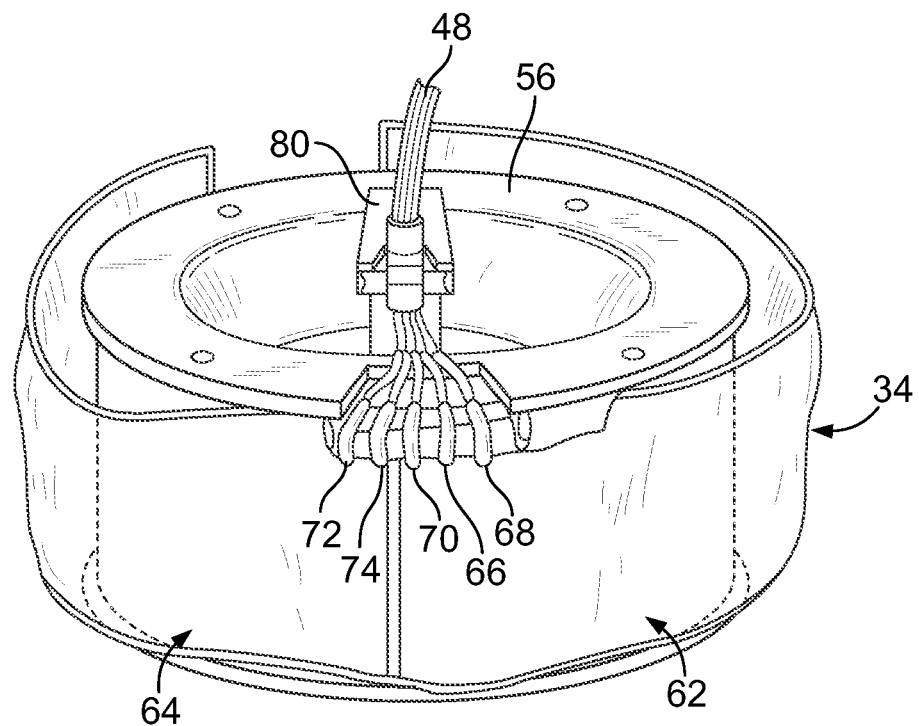
FIG. 5 is a top perspective view of the spool of the centrifuge system of FIG. 4 in its upright position and carrying the blood separation chamber of the flow circuit of FIG. 2.

As FIGS. 5 and 6 best show, there are three ports 66, 68, and 70 associated with the first stage 62. Depending on the particular blood processing procedure, the ports may have different functionality but, in a therapeutic plasma exchange procedure, the port identified at 70 is used for conveying blood from a blood source into the first stage 62 (via tubing 32 of the flow circuit 12). During such a therapeutic plasma exchange procedure, the other two ports 66 and 68 serve as outlet ports for passing separated blood components from the first stage 62 to the flow circuit 12 (via tubing 36 and 38, respectively). More particularly, the first outlet port 68 conveys a low density blood component from the first stage 62, while the second outlet port 66 conveys a high density blood component from the first stage 62.

In a method of carrying out single-stage processing, one of the separated components is returned to the blood source, while the other is removed from the first stage 62 for further processing via an adsorption device, as will be described in greater detail herein. For example, when carrying out a therapeutic plasma exchange procedure, whole blood in the first stage 62 is separated into cellular components (i.e., a high density component) and substantially cell-free plasma (i.e., a low density component). The plasma is removed from the first stage 62 via the first outlet port 68 for further processing by the adsorption device, while the cellular components are removed from the first stage 62 via the second outlet port 66 and returned to the blood source. After the plasma has been treated by the adsorption device, it may be returned to the blood source, as will be described in greater detail herein.

If multi-stage processing is required, one of the components will be transferred from the first stage 62 to the second stage 64 via a port 72 associated with the second stage 64. The component transferred to the second stage 64 is further fractionated into sub-components, with one of the sub-components being removed from the second stage 64 via an outlet port 74 and the other sub-component remaining in the second stage 64. In the illustrated embodiment, the ports 66, 68, 70, 72, and 74 are arranged side-by-side along the top transverse edge of the chamber 34.

While the same ports 66, 68, and 70 of the first stage 62 are used as in the above-described therapeutic plasma exchange procedure, the ports 66 and 70 have different functionality in a multi-stage separation procedure. In one method of multi-stage operation, blood enters the first stage 62 via the port 66 and is separated into red blood cells (i.e., the high density blood component) and platelet-rich plasma (i.e., the low density blood component). The red blood cells are returned to the blood source (via the port 70), while the platelet-rich plasma is conveyed out of the first stage 62 (via the first outlet port 68) and into the second stage 64 (via the inlet port 72). In the second stage 64, the platelet-rich plasma is separated into platelet-poor plasma and platelet concentrate. The platelet-poor plasma is removed from the second stage 64 (via the outlet port 74), leaving platelet concentrate in the second stage 64 for resuspension and transfer to one or more storage containers.

As best shown in FIG. 5, the tubing umbilicus 48 of the flow circuit 12 is attached to the ports 66, 68, 70, 72, and 74. The umbilicus 48 interconnects the first and second stages 62 and 64 with each other and with the components of the flow circuit 12 positioned outside of the centrifuge 52. As FIG. 3 shows, a non-rotating (zero omega) holder 76 holds the upper portion of the umbilicus 48 in a non-rotating position above the spool 56 and bowl 54. A holder 78 on the yoke 58 rotates the mid-portion of the umbilicus 48 at a first (one omega) speed about the suspended spool 56 and bowl 54. Another holder 80 (FIGS. 4 and 5) rotates the lower end of the umbilicus 48 at a second speed twice the one omega speed (the two omega speed), at which speed the spool 56 and bowl 54 also rotate. This known relative rotation of the umbilicus 48 keeps it untwisted, in this way avoiding the need for rotating seals.

As FIG. 6 shows, a first interior seal 82 is located between the low density outlet port 68 and the high density outlet port 66. A second interior seal 84 is located between the high density outlet port 66 and the blood inlet port 70. The interior seals 82 and 84 form a fluid passage 86 (an outlet for high density blood components in a therapeutic plasma exchange procedure) and a low density collection region 88 in the first stage 62. The second seal 84 also forms a fluid passage 90 (a blood inlet in a therapeutic plasma exchange procedure) in the first stage 62.

C. The Cassettes

Blood entering the blood separation chamber 34 is pumped thereinto by one or more pumps 92 of the centrifuge system 10 (FIGS. 1 and 2) acting upon one or more of the tubing loops 50 extending from the cassettes 16-16b of the flow circuit 12 (FIG. 2). An exemplary cassette 16 is illustrated in greater detail in FIGS. 7 and 8, while the pumps 92 and associated cassette holder 94 are shown in greater detail in FIG. 9.

Before beginning a given blood processing and collection procedure, the operator loads various components of the flow circuit 12 onto the sloped front panel 96 and centrifuge 52 of the centrifuge system 10. As described above, the blood separation chamber 34 and the umbilicus 48 of the flow circuit 12 are loaded into the centrifuge 52, with a portion of the umbilicus 48 extending outside of the interior of the centrifuge system 10, as shown in FIG. 3. The sloped front panel 96 of the centrifuge system 10 includes at least one cassette holder 94 (three in the illustrated embodiment), each of which is configured to receive and grip an associated cassette 16-16b of the flow circuit 12.

Figure 7:
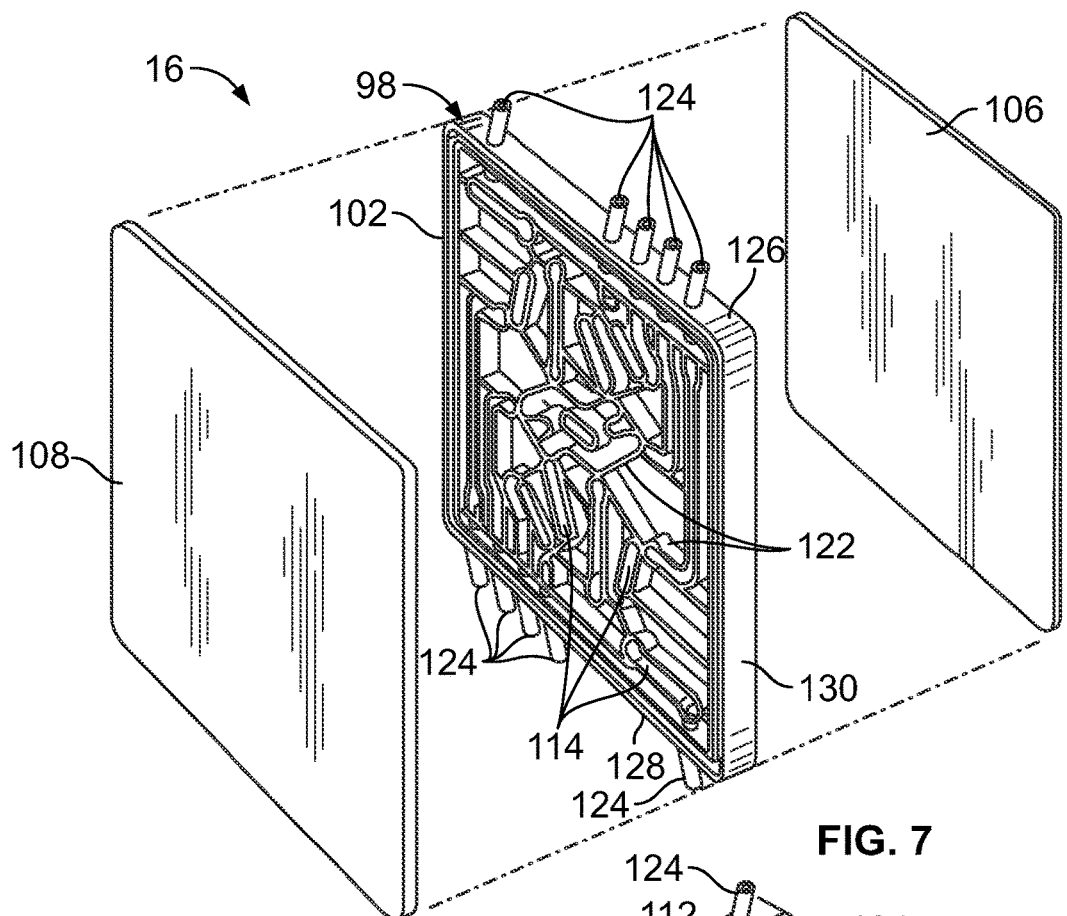
FIG. 7 is an exploded perspective view of a fluid processing cassette of the flow circuit of FIG. 2.
Figure 8:
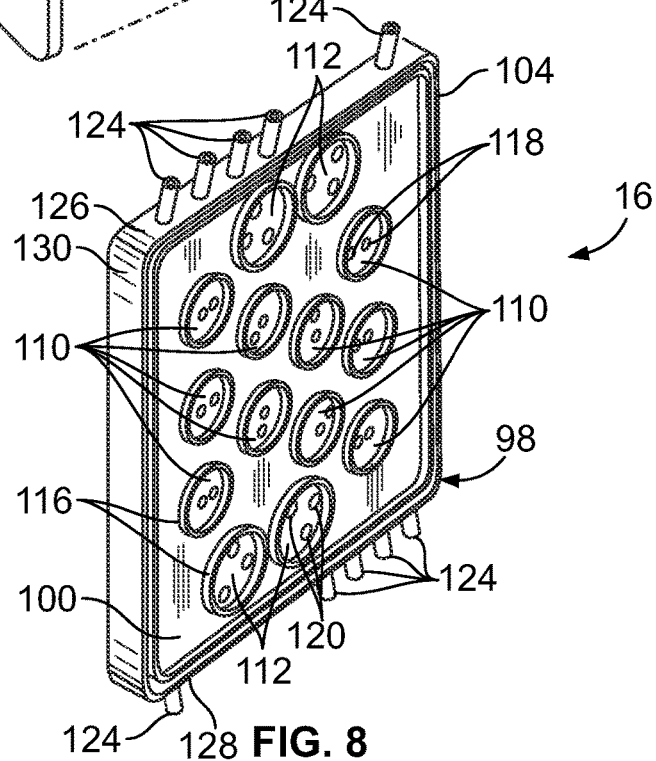
FIG. 8 is a perspective view of an underside of the fluid processing cassette of FIG. 7.
Figure 9:
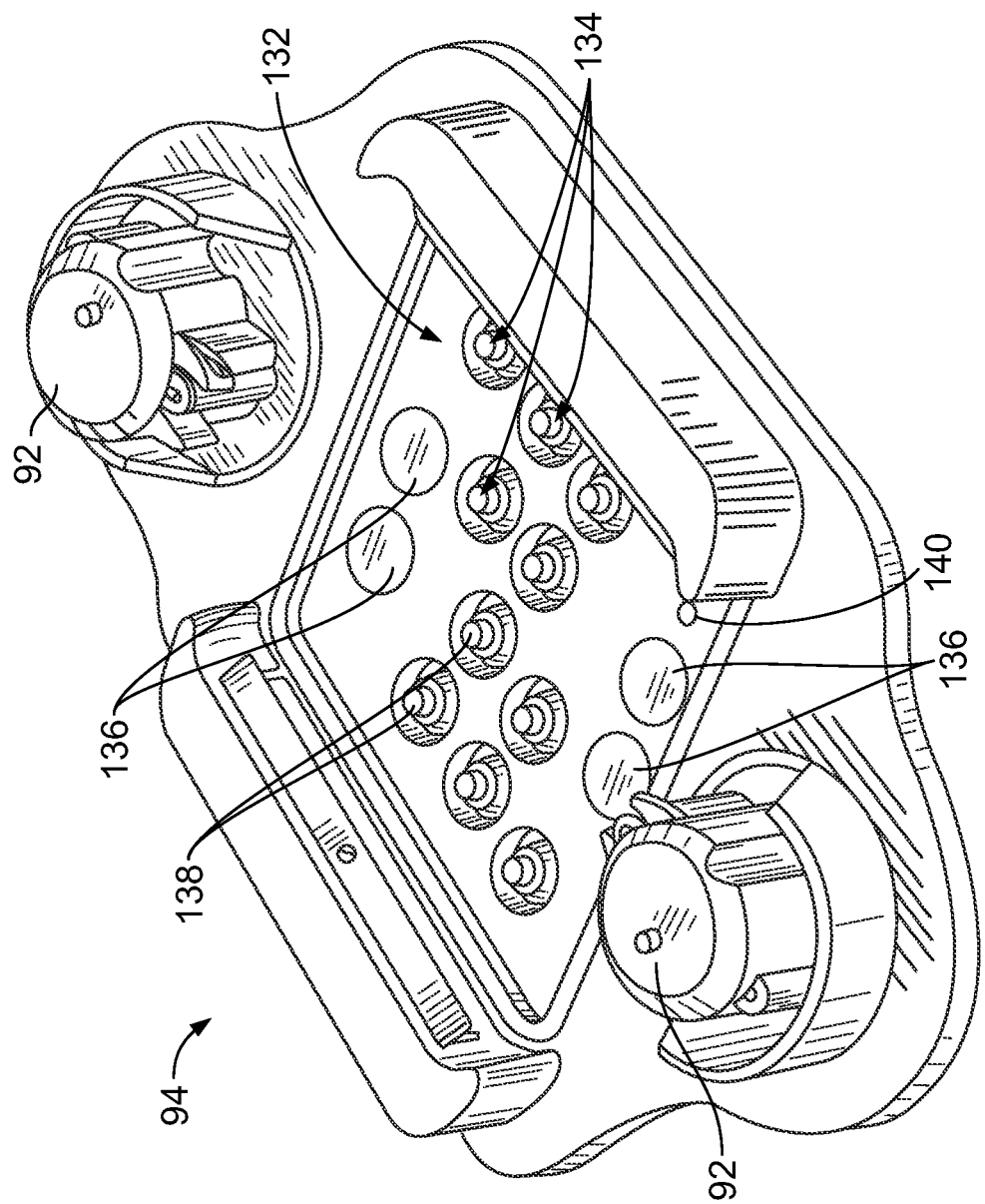
FIG. 9 is a perspective view of a cassette holder of the centrifuge system of FIG. 1.

Each cassette 16-16b, one of which is shown in FIGS. 7 and 8, includes an injection molded body 98 that is compartmentalized by an interior wall 100 (FIG. 8) to present or form a topside 102 (FIG. 7) and an underside 104 (FIG. 8). For the purposes of description, the topside 102 is the side of the cassette 16 that, in use, faces away from the centrifuge system 10, while the underside 104 faces towards the centrifuge system 10. A flexible diaphragm 106 overlies and peripherally seals the underside 104 of the cassette 16. A generally rigid upper panel 108 overlies the topside 102 of the cassette 16 and is sealed peripherally and to the raised channel-defining walls in the cassette 16, as described later.

In one embodiment, the cassette 16, the interior wall 100, and the upper panel 108 are made of a rigid medical grade plastic material, while the diaphragm 106 is made of a flexible sheet of medical grade plastic. The upper panel 108 and the diaphragm 106 are sealed about their peripheries to the peripheral edges of the top- and undersides 102, 104 of the cassette 16, respectively.

As shown in FIGS. 7 and 8, the top- and undersides 102, 104 of the cassette 16 contain preformed cavities. On the underside 104 of the cassette 16 (FIG. 8), the cavities form an array of valve stations 110 and an array of pressure sensing stations 112. On the topside 102 of the cassette 16 (FIG. 7), the cavities form an array of channels or paths 114 for conveying liquids. The valve stations 110 communicate with the liquid paths 114 through the interior wall 100 to interconnect them in a predetermined manner. The sensing stations 112 also communicate with the liquid paths 114 through the interior wall 100 to sense pressures in selected regions. The number and arrangement of the liquid paths 114, the valve stations 110, and the sensing stations 112 can vary but, in the illustrated embodiment, the cassette 16 provides nineteen liquid paths 114, ten valve stations 110, and four sensing stations 112.

The valve and sensing stations 110, 112 resemble shallow wells open on the cassette underside 104 (FIG. 8). Upstanding edges 116 rise from the interior wall 100 and peripherally surround the valve and sensing stations 110, 112. The valve stations 110 are closed by the interior wall 100 on the topside 102 of the cassette 16, except that each valve station 110 includes a pair of through holes or ports 118 in the interior wall 100. The ports 118 each open into selected different liquid paths 114 on the topside 102 of the cassette 16.

The sensing stations 112 are likewise closed by the interior wall 100 on the topside 102 of the cassette 16, except that each sensing station 112 includes three through holes or ports 120 in the interior wall 100 (FIG. 8). The ports 120 open into selected liquid paths 114 on the topside 102 of the cassette 16. These ports 120 channel liquid flow among the selected liquid paths 114 through the associated sensing station 112.

In one embodiment, the flexible diaphragm 106 overlying the underside 104 of the cassette 16 is sealed by ultrasonic welding to the upstanding peripheral edges 116 of the valve and sensing stations 110, 112. This isolates the valve stations 110 and sensing stations 112 from each other and the rest of the system. In an alternative embodiment, the flexible diaphragm 106 can be seated against the upstanding edges 116 by an external positive force applied by the cassette holder 94 against the diaphragm 106. The positive force, like the ultrasonic weld, peripherally seals the valve and sensing stations 110, 112.

The localized application of additional positive force (referred to herein as a "closing force") upon the intermediate region of the diaphragm 106 overlying a valve station 110 serves to flex the diaphragm 106 into the valve station 110. Such closing force is provided by the cassette holder 94, as will be described in greater detail herein. The diaphragm 106 seats against one of the ports 118 to seal the port 118, which closes the valve station 110 to liquid flow. Upon removal of the closing force, fluid pressure within the valve station 110, the application of a vacuum to the outer surface of the diaphragm 106, and/or the plastic memory of the diaphragm 106 itself unseats the diaphragm 106 from the port 118, opening the valve station 110 to liquid flow.

Upstanding channel sides or edges 122 rise from the interior wall 100 to peripherally surround and define the liquid paths 114, which are open on the topside 102 of the cassette 16. The liquid paths 114 are closed by the interior wall 100 on the underside 104 of the cassette 16, except for the ports 118, 120 of the valve and sensing stations 110, 112 (FIG. 8). The rigid panel 108 overlying the topside 102 of the cassette 16 is sealed by ultrasonic welding to the upstanding peripheral edges 122, sealing the liquid paths 114 from each other and the rest of the system.

In the illustrated embodiment, ten pre-molded tube connectors 124 extend out along opposite side edges 126, 128 of each cassette 16. The tube connectors 124 are arranged five on one side edge 126 and five on the other side edge 128. The other side edges 130 of the cassette 16, as illustrated, are free of tube connectors. The tube connectors 124 are associated with external tubing (FIG. 2) to associate the cassettes 16 with the remainder of the flow circuit 12, as described above.

The tube connectors 124 communicate with various interior liquid paths 114, which constitute the liquid paths of the cassette 16 through which a fluid enters or exits the cassette 16. The remaining interior liquid paths 114 of the cassette 16 constitute branch paths that link the liquid paths 114 associated with the tube connectors 124 to each other through the valve stations 110 and sensing stations 112.

D. The Cassette Holders and Pumps

Turning now to the cassette holders 94 (FIG. 9), each receives and grips one of the cassettes 16-16b along the two opposed sides edges 130 in the desired operating position. The cassette holder 94 includes a pair of peristaltic pump stations 92. When the cassette 16 is gripped by the cassette holder 94, tubing loops 50 extending from the cassette 16 (FIG. 2) make operative engagement with the pump stations 92. The pump stations 92 are operated to cause fluid flow through the cassette 16.

The flexible diaphragm 106 covering the underside 104 of the cassette 16 is urged into intimate contact with a valve and sensor array or assembly 132 by the cassette holder 94. The valve assembly 132 acts in concert with the valve stations 110 and sensing stations 112 of the cassette 16. The valve assembly 132 illustrated in FIG. 9 includes ten valve actuators 134 and four pressure sensing transducers 136. The valve actuators 134 and the pressure sensing transducers 136 are mutually arranged in the same layout as the valve stations 110 and sensing stations 112 on the underside 104 of the cassette 16. When the cassette 16 is gripped by the cassette holder 94, the valve actuators 134 align with the cassette valve stations 110. At the same time, the pressure sensing transducers 136 mutually align with the cassette sensing stations 112.

In one embodiment, each valve actuator 134 includes an electrically actuated solenoid pin or piston 138. Each piston 138 is independently movable between an extended position and a retracted position. When in its extended position, the piston 138 presses against the region of the diaphragm 106 that overlies the associated valve station 110. In this position, the piston 138 flexes the diaphragm 106 into the associated valve station 110, thereby sealing the associated valve port 118. This closes the valve station 110 to liquid flow. When in its retracted position, the piston 138 does not apply force against the diaphragm 106. As before described, the plastic memory of the diaphragm 106 may be such that the removal of force is sufficient for the diaphragm to unseats from the valve port 118, thereby opening the valve station 110 to liquid flow. Alternatively, a vacuum may be applied to the diaphragm 106, for example by the vacuum port 140 illustrated in FIG. 9, to actively unseat the diaphragm 106 from the valve port 118.

The pressure sensing transducers 136 sense liquid pressures in the sensing stations 112 of the cassette 16. The sensed pressures are transmitted to a controller of the centrifuge system 10 as part of its overall system monitoring function. If provided, the vacuum port 140 of the cassette holder 94 may provide suction to the diaphragm 106 of the cassette 16, drawing it into close contact with the transducers 136 for more accurate pressure readings.

E. Blood Separation

As described above, the centrifuge 52 rotates the blood separation chamber 34, thereby centrifugally separating whole blood received from a blood source into component parts, e.g., red blood cells, plasma, and buffy coat comprising platelets and leukocytes.

Figure 10:
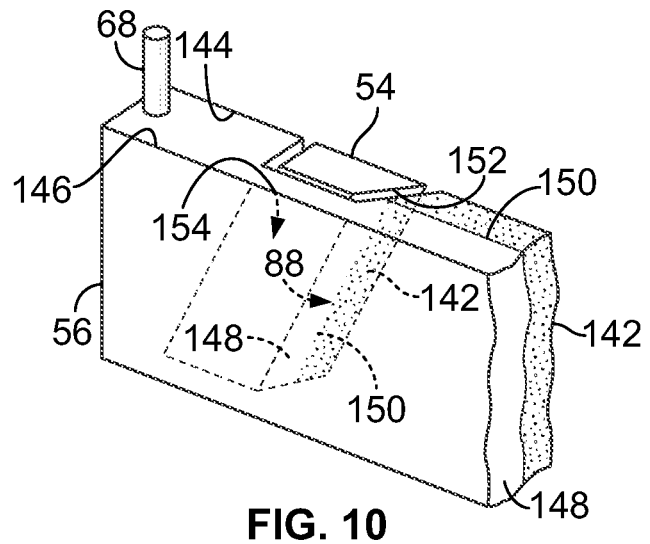
FIG. 10 is an enlarged perspective view of an interface ramp carried by the centrifuge in association with the blood separation chamber, showing the centrifugally separated red blood cell layer, plasma layer, and interface within the chamber when in a desired location on the ramp.

In a therapeutic plasma exchange procedure, the fluid passage 90 channels blood directly into the circumferential flow path immediately next to the low density collection region 88. As shown in FIG. 10, the blood separates into an optically dense layer 142 containing cellular components, which forms as cellular components move under the influence of centrifugal force toward the high-G (outer) wall 144. The optically dense layer 142 will include red blood cells (and, hence, will be referred to herein as the "RBC layer") but, depending on the speed at which the centrifuge 52 is spun, other cellular components (e.g., larger white blood cells and platelets) may also be present in the RBC layer 142.

The movement of the component(s) of the RBC layer 142 displaces less dense blood components radially toward the low-G (inner) wall 146, forming a second, less optically dense layer 148. The less optically dense layer 148 includes plasma (and, hence, will be referred to herein as the "plasma layer") but, depending on the speed at which the centrifuge 52 is rotated and the length of time that the blood is resident in the centrifuge, other components (e.g., platelets and smaller white blood cells) may also be present in the plasma layer 148.

The transition between the formed cellular blood components and the liquid plasma component is generally referred to as the interface 150 (FIG. 10). Platelets and white blood cells (which have a density greater than plasma and usually less than red blood cells) typically occupy this transition region, although that also varies with centrifuge speed and residence time, as is well known in the technical field.

Figure 11:
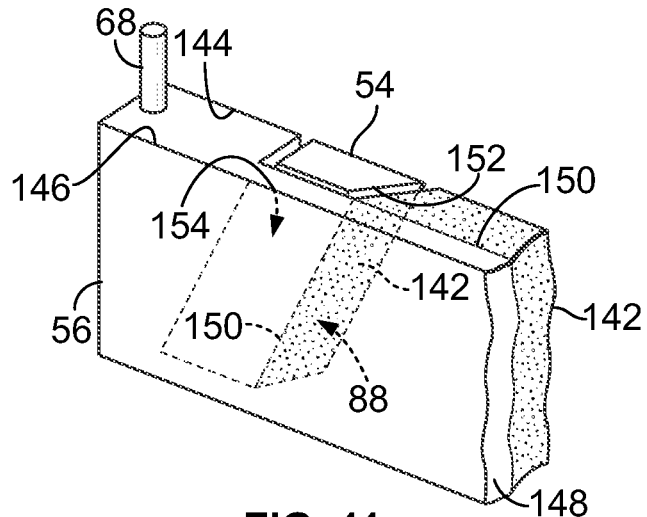
FIG. 11 is an enlarged perspective view of the interface ramp shown in FIG. 10, showing the red blood cell layer and interface at an undesired high location on the ramp.
Figure 12:
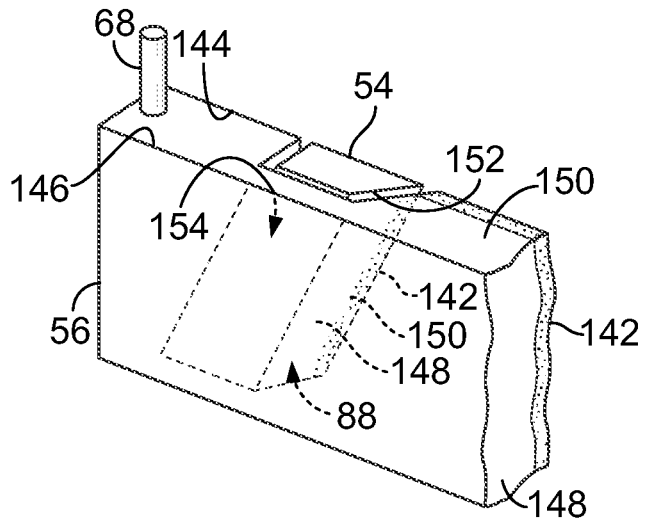
FIG. 12 is an enlarged perspective view of the interface ramp shown in FIG. 10, showing the red blood cell layer and interface at an undesired low location on the ramp.

The location of the interface 150 within the chamber 34 can dynamically shift during blood processing, as FIGS. 11 and 12 show. If the location of the interface 150 is too high (that is, if it is too close to the low-G wall 146 and the removal port 68, as FIG. 11 shows), cellular components can spill over and into the low density collection region 88, adversely affecting the quality of the low density components (typically plasma). On the other hand, if the location of the interface 150 is too low (that is, if it resides too far away from the low-G wall 146, as FIG. 12 shows), the collection efficiency of the centrifuge system 10 may be impaired.

As FIG. 10 shows, a ramp 152 extends from the high-G wall 144 of the bowl 54 at an angle across the low density collection region 88. The angle, measured with respect to the axis of the first outlet port 68 is about 30° in one embodiment. FIG. 10 shows the orientation of the ramp 88 when viewed from the low-G wall 146 of the spool 56. FIG. 6 shows, in phantom lines, the orientation of the ramp 152 when viewed from the high-G wall 144 of the bowl 54.

Further details of the angled relationship of the ramp 152 and the first outlet port 68 can be found in U.S. Pat. No. 5,632,893 to Brown et al., which is incorporated herein by reference.

The ramp 152 forms a tapered wedge that restricts the flow of fluid toward the first outlet port 68. The top edge of the ramp 152 extends to form a constricted passage 154 along the low-G wall 146. The plasma layer 148 must flow through the constricted passage 154 to reach the first outlet port 68.

As FIG. 10 shows, the ramp 152 makes the interface 150 between the RBC layer 142 and the plasma layer 148 more discernible for detection, displaying the RBC layer 142, plasma layer 148, and interface 150 for viewing through the high-G wall 144 of the chamber 34.

It may be advantageous for the centrifuge 52 to include a second projection (in addition to the ramp 152), which interacts with the first stage 62 of the blood separation chamber 34. As the ramp 152 extends across the path leading to the first outlet port 68, a second projection may extend across the path leading to the second outlet port 66 to prevent plasma from flowing into the second outlet port 66 instead of the first outlet port 68. An exemplary centrifuge incorporating a second projection which helps regulate fluid flow in the first stage of a multiple-stage blood separation chamber is described in greater detail in U.S. provisional patent application No. 61/474,951, filed Apr. 13, 2011, which is incorporated herein by reference.

Further details of the separation chamber 34 and its operation may be found in U.S. Pat. No. 5,316,667, which is incorporated by reference.

F. The Interface Controller

The interface controller is functional to determine the location of the interface 150 on the ramp 152 and, if the interface 150 is located at an improper location (e.g., in the locations of FIG. 11 or 12), to correct the location of the interface 150.

Figure 13:
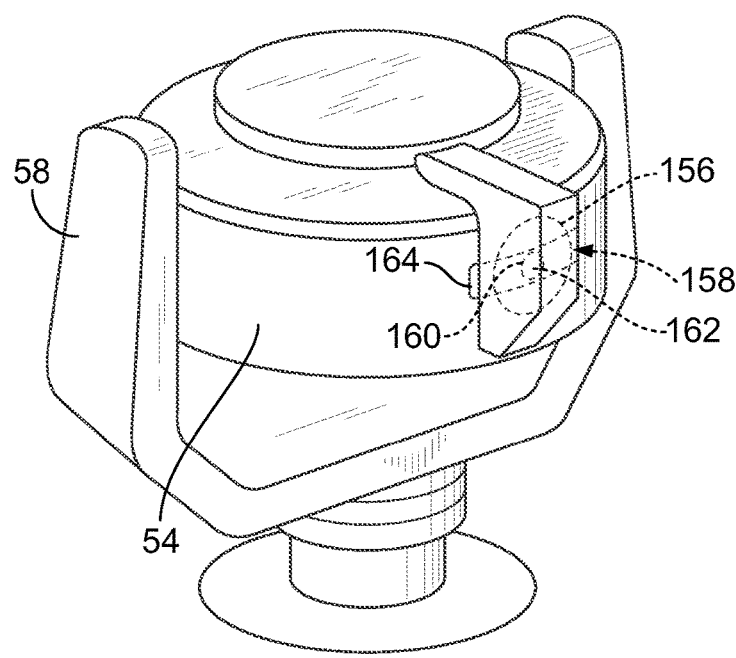
FIG. 13 is a side perspective view of the centrifuge bowl and spool of the centrifuge system when in the operating position, showing a viewing head, which forms a part of the interface controller, being carried by the centrifuge to view the interface ramp during rotation of the centrifuge bowl.
Figure 14:
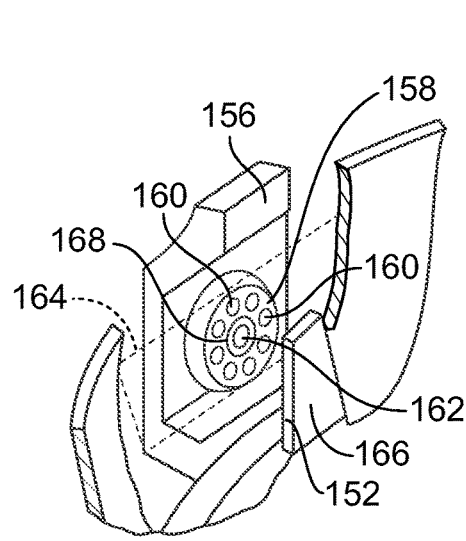
FIG. 14 is a perspective view of the viewing head, with portions broken away and in section, showing the light source and light detector, which are carried by the viewing head, in alignment with the interface ramp, as viewed from within the spool and bowl of the centrifuge.
Figure 15:
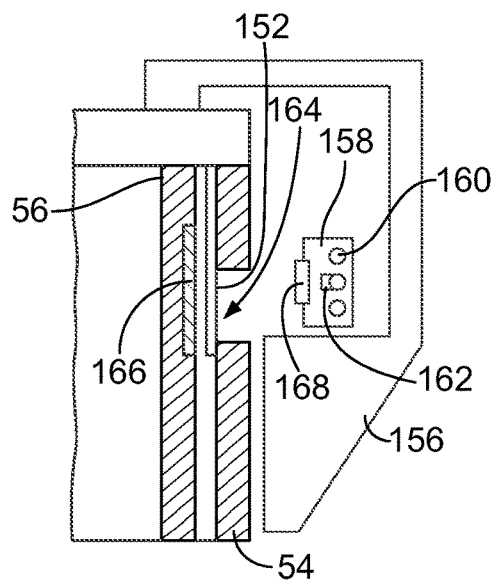
FIG. 15 is a side section view of the bowl, spool, and viewing head when the viewing head is aligned with the interface ramp.

The interface controller includes a viewing head 156 carried on the yoke 58 (see FIGS. 3 and 13). The viewing head 156 is oriented to optically view the transition in optical density between the RBC layer 142 and the plasma layer 148 on the ramp 152. Referring to FIGS. 13-15, the viewing head 156 includes a light source 158, which emits light that is absorbed by red blood cells. In the illustrated embodiment, the light source 158 includes a circular array of red light emitting diodes 160, but other wavelengths absorbed by red blood cells, like green or infrared, could also be used.

In the illustrated embodiment, seven light emitting diodes 160 comprise the light source 158. More diodes 160 may be used, or fewer diodes 160 can be used, depending upon the optical characteristics desired. Further, non-LED lights may also be employed without departing from the scope of the present disclosure.

The viewing head 156 also includes a light detector 162 (FIGS. 14 and 15), which is mounted adjacent to the light source 158. In one embodiment, the light detector 162 comprises a PIN diode detector, which is located generally in the geometric center of the circular array of light emitting diodes 160. Other types of light detectors may also be employed.

The yoke 58 and the viewing head 156 rotate at a one omega speed, as the spool 56 and bowl 54 rotate at a two omega speed. The light source 158 directs light onto the rotating bowl 54. In the illustrated embodiment, the bowl 54 is transparent to the light emitted by the source 158 only in the region 164 where the bowl 54 overlies the interface ramp 152 (FIG. 13). In the illustrated embodiment, the region 164 comprises a window cut out in the bowl 54. The remainder of the bowl 54 that lies in the path of the viewing head 156 comprises an opaque or light absorbing material.

The interface ramp 152 is made of a light transmissive material. The light from the source 158 will thereby pass through the transparent region 164 of the bowl 54 and the ramp 152 every time the rotating bowl 54 and viewing head 156 align. The spool 56 may also carry a light reflective material 166 (FIGS. 14 and 15) behind the interface ramp 152 to enhance its reflective properties. The spool 56 reflects incoming light received from the source 158 out through the transparent region 164 of the bowl 54, where it is sensed by the detector 162. In the illustrated embodiment, light passing outward from the source 158 and inward toward the detector 162 passes through a focusing lens 168 (shown in FIGS. 14 and 15), which forms a part of the viewing head 156.

Such an arrangement optically differentiates the reflective properties of the interface ramp 152 from the remainder of the bowl 54. This objective can be achieved in other ways. For example, the light source 158 could be gated on and off with the arrival and passage of the ramp 152 relative to its line of sight. As another example, the bowl 54 outside the transparent region 164 could carry a material that reflects light, but at a different intensity than the reflective material 166 behind the interface ramp 152.

As the transparent region 164 of the bowl 54 comes into alignment with the viewing head 156, the detector 162 will first sense light reflected through the plasma layer 148 on the ramp 152. Eventually, the RBC layer 142 adjacent the interface 150 on the ramp 152 will enter the optical path of the viewing head 156. The RBC layer 142 absorbs light from the source 158 and thereby reduces the previously sensed intensity of the reflected light. The intensity of the reflected light sensed by the detector 162 represents the amount of light from the source 158 that is not absorbed by the RBC layer 142 adjacent to the interface 150. With this information, a processing element or module can determine the location of the interface 150 on the ramp 152 relative to the constricted passage 154. A more detailed discussion of the algorithms by which the interface controller receives and processes signals to determine the location of the interface 150 on the ramp 152 may be found in U.S. Pat. No. 6,312,607 to Brown et al., which is incorporated herein by reference.

When the location of the interface 150 on the ramp 152 has been determined, the processing element outputs that information to an interface command element or module. The command element includes a comparator, which compares the interface location output with a desired interface location to generate an error signal. The error signal may take a number of forms but, in one embodiment, is expressed in terms of a targeted red blood cell percentage value (i.e., the percentage of the ramp 152 which should be occupied by the RBC layer 142).

When the control value is expressed in terms of a targeted red blood cell percentage value, a positive error signal indicates that the RBC layer 142 on the ramp 152 is too large (as FIG. 11 shows). The interface command element generates a signal to adjust an operational parameter accordingly, such as by reducing the rate at which plasma is removed through the first outlet port 68 under action of one or more of the pumps 92. The interface 150 moves away from the constricted passage 154 toward the desired control position (as FIG. 10 shows), where the error signal is zero.

A negative error signal indicates that the RBC layer 142 on the ramp 152 is too small (as FIG. 12 shows). The interface command element generates a signal to adjust an operational parameter accordingly, such as by increasing the rate at which plasma is removed through the first outlet port 68. The interface 150 moves toward the constricted passage 154 to the desired control position (FIG. 10), where the error signal is again zero.

G. Adsorption Device

As noted above, in an exemplary therapeutic plasma exchange operation, plasma is separated from cellular blood components in the first stage 62 of the blood separation chamber 34 and returned to the flow circuit 12 via the first outlet port 68 for further processing via an adsorption device. Although the operation may differ depending on the device, an adsorption device typically operates by providing a ligand or binding agent on a substrate. The substrate is packed into a housing (typically in the form of a column) and plasma is passed through the housing so as to come into contact with the substrate. The ligand binds to a particular substance (or substances) in the plasma, thereby removing the substance(s) from the plasma. The nature of the ligand depends on the substance(s) to be removed from the plasma. In known adsorption devices, antibodies and/or immune complexes may be removed from plasma using peptide-GAM or protein A as a ligand, while in other known devices, selected lipoproteins may be removed from plasma using dextran sulfate as a ligand. Other ligands may also be employed without departing from the scope of the present disclosure. Methods of selecting a ligand and preparing and using an adsorption device are described in U.S. Pat. No. 5,277,701 to Christie et al., which is incorporated herein by reference.

Any of a variety of adsorption devices may be employed in combination with the blood separation system, including (but not limited to) the Globaffin™ and Immunosorba™ devices from Fresenius Medical Care Deutschland GmbH of Bad Homburg, Germany and the Liposorber® device from Kaneka Corporation of Osaka, Japan.

Figure 16:
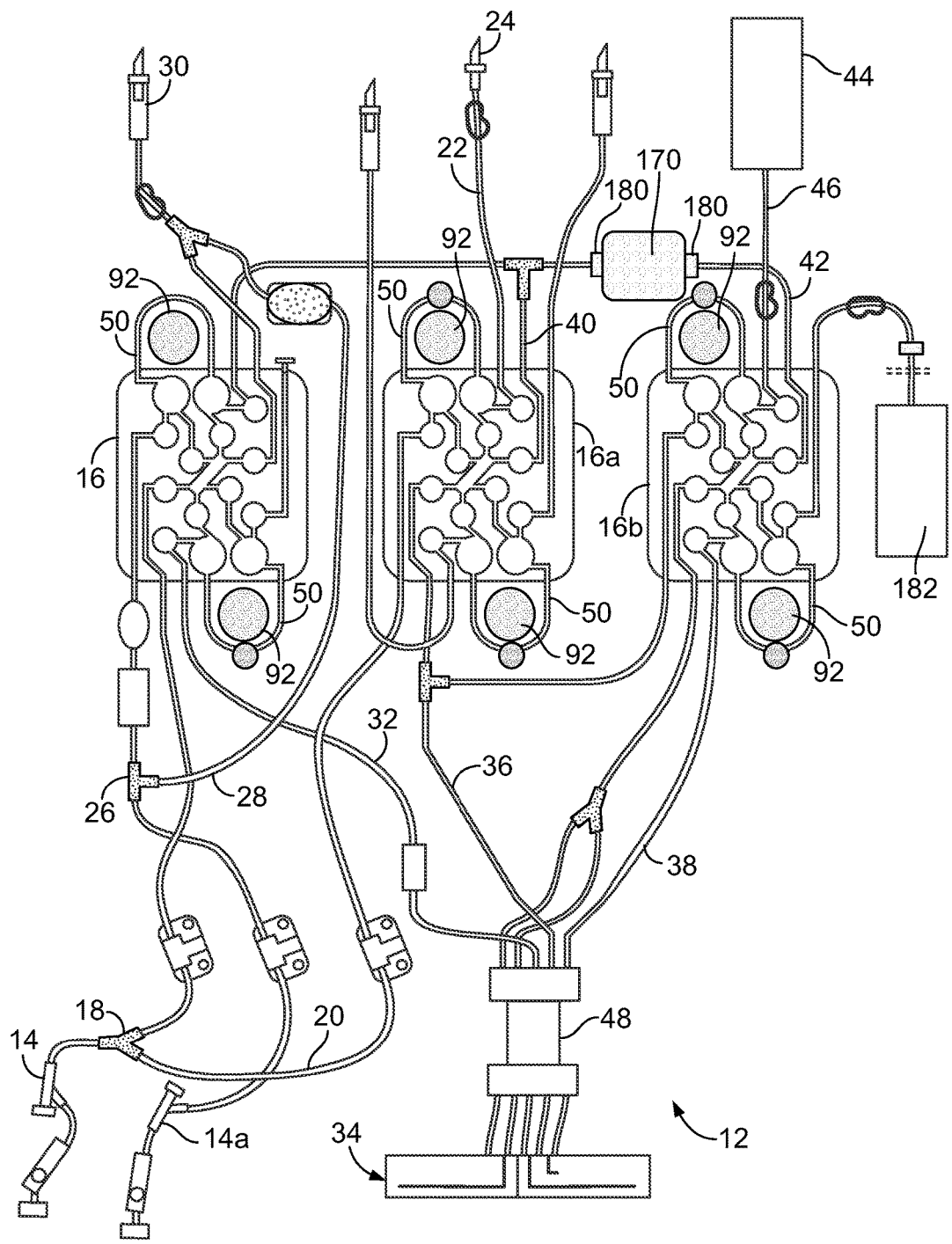
FIG. 16 is a diagrammatic view of one embodiment of the flow circuit of FIG. 2 incorporating an adsorption device.
Figure 17:
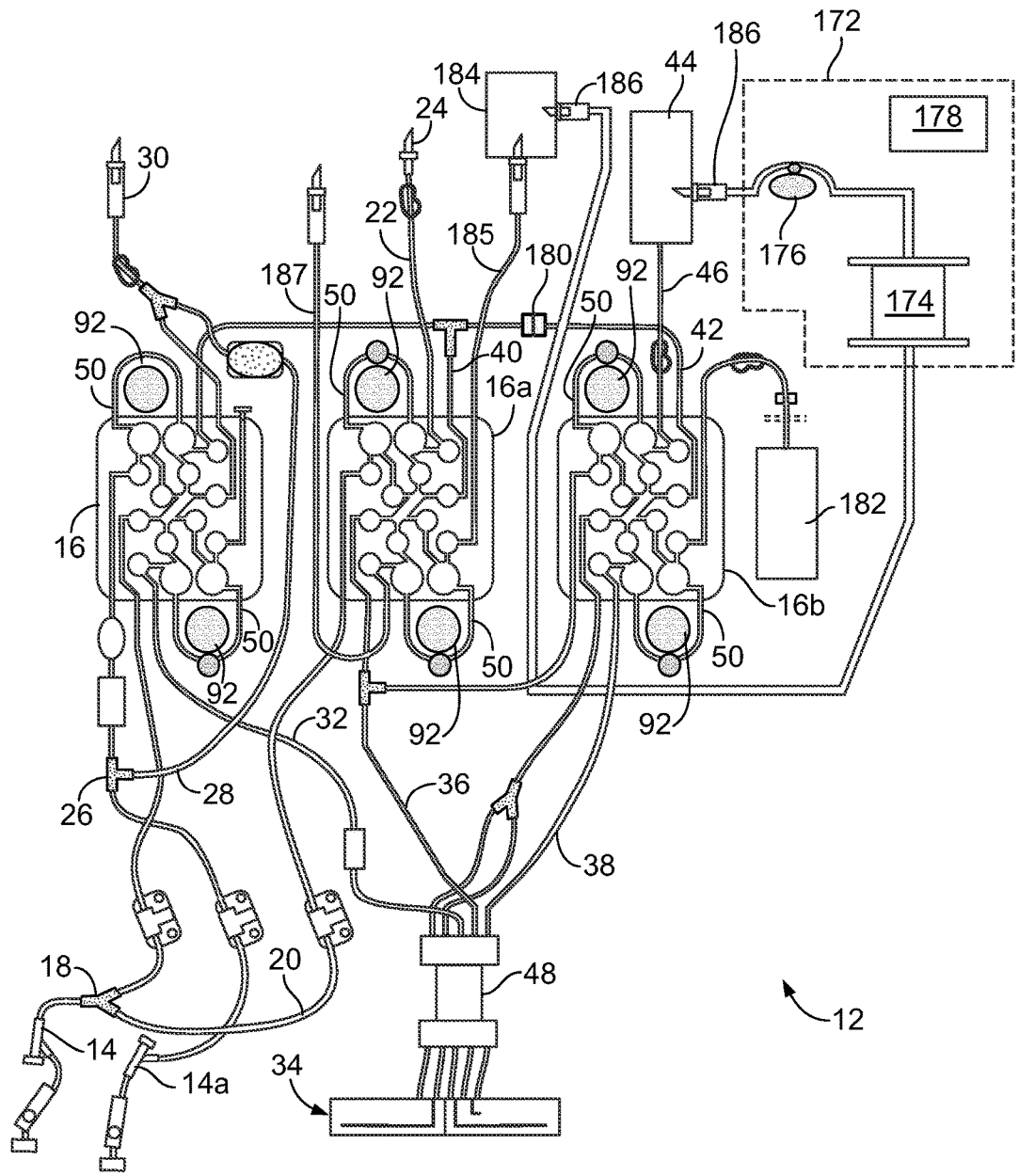
FIG. 17 is a diagrammatic view of an alternative embodiment of the flow circuit of FIG. 2 incorporating an adsorption device.

The adsorption device may be variously connected to the blood separation system, such as in what may be referred to a "passive" blood treatment system (FIG. 16) or in what may be referred to as an "active" blood treatment system (FIG. 17). In a passive system, the adsorption device consists solely of an adsorption column (or the like) for removing undesirable substances from separated plasma by adsorption. In an active system, the adsorption device 172 includes a variety of components, including an adsorption column 174 (or the like) for removing undesirable substances, a fluid flow element 176, and a controller 178.

1. Passive Blood Treatment System

The flow circuit 12 of FIG. 2 (also shown in FIG. 16) is illustrated with tubing 42 connected to the right cassette 16b. The tubing 42 includes a connector 180 which allows a downstream portion of the tubing 42 to be selectively disconnected from an upstream portion of the tubing 42. In one embodiment, the connector 180 comprises a luer connector, which includes male and female mating parts which may be selectively connected and disconnected from one another, although a differently configured connector may also be employed without departing from the scope of the present disclosure.

In a passive system, the mating parts of the connector 180 are separated to disconnect the downstream and upstream portions of the tubing 42 and then the mating parts are connected to the adsorption device 170 to fluidly connect the adsorption device or column 170 inline with the downstream and upstream portions of the tubing 42, as shown in FIG. 16. Typically, this is done before a blood source is connected to the flow circuit 12 and before blood separation begins. It may be advantageous for the adsorption device 170 to be primed before it is connected to the flow circuit 12.

After the plasma is separated from the anticoagulated whole blood, it is pumped from the blood separation chamber 34 into the right cassette 16b via tubing 38. The plasma is routed through the right cassette 16b and exits via tubing 42, to flow through the adsorption device 170. As the adsorption device 170 does not include its own pump or fluid flow element, the plasma is pumped into, through, and out of the adsorption device 170 by one or more of the pump(s) of the centrifuge system 10. In the illustrated embodiment, the lower pump 92 associated with the right cassette 16b pumps plasma out of the right cassette 16b and through the adsorption device 170, and is referred to herein as the "plasma pump" of the passive system. Other pumping and fluid flow arrangements may also be employed without departing from the scope of the present disclosure.

The adsorption device 170 receives the separated plasma from the blood separation system and processes it to remove undesirable substances by adsorption. The processed plasma flows out of the adsorption device 170 and back into the flow circuit 12 of the blood separation system, where it may be returned to the blood source.

A given adsorption device will be capable of processing only a certain amount of fluid, above which amount the adsorption device may become clogged or non-functional. Typically, the maximum amount of fluid which may be processed is expressed in terms of the maximum flow rate of fluid flowing into the adsorption device and/or the pressure of fluid flowing into the adsorption device. Therefore, when a "passive" blood treatment protocol has been selected by an operator (e.g., using a touch screen user interface or the like), to ensure that an excessive amount of plasma is not pumped into the adsorption device 170, the controller of the centrifuge system 10 may require the operator to input processing parameters specifying the maximum flow rate and/or maximum pressure of fluid pumped into the adsorption device 170. Alternatively, rather than prompting the operator to enter the processing parameters, the controller may be pre-programmed with a maximum flow rate and/or maximum pressure for the associated adsorption device 170. The controller may also provide the operator with instructions for connecting the adsorption device 170 to the flow circuit 12 and then perform integrity checks to help ensure that the adsorption device 170 is properly connected. This is also applicable to the active blood treatment system and the adsorption device 172 employed therein.

The plasma pump(s) of the centrifuge system 10 flows plasma into the adsorption device 170 at an actual flow rate and an actual pressure. As described previously, the cassettes (including the right cassette 16b) include a number of sensing stations 112 capable of determining the pressure in various regions of the cassette, which information may be used to determine the actual flow rate and/or pressure of plasma flowing into the adsorption device 170. Others means for determining the actual flow rate and/or actual pressure (e.g., using scales to measure the weight of fluid in different locations of the flow circuit 12) may also or alternatively be employed without departing from the scope of the present disclosure.

The actual flow rate and actual pressure of plasma entering into the adsorption device 170 may be automatically compared to the maximum flow rate and/or maximum pressure by the controller of the centrifuge system 10. If the actual flow rate equals or exceeds the maximum flow rate, the controller may command the plasma pump(s) to flow plasma into the adsorption device 170 at a lower flow rate. If the actual pressure equals or exceeds the maximum pressure, the controller may make similar adjustments to decrease the actual pressure to a suitable level. By way of example, the illustrated flow circuit 12 includes a vent container 182 associated with the right cassette 16b. Fluid communication between the vent container 182 and the remainder of the flow circuit 12 may be manually controlled or selectively established (under command of the controller) to decrease the pressure of fluid flowing into the adsorption device 170. Other regions of the flow circuit 12, including container 44 may also serve as venting means without departing from the scope of the present disclosure. This is also applicable to the active blood treatment system and the adsorption device 172 employed therein.

When it detects an elevated flow rate or pressure, the controller may take other actions in addition to remedial ones. For example, the controller may command an alarm to be triggered, thereby alerting an operator to the high flow rate and/or pressure. The controller may give the operator the option of canceling the procedure in the event of an alarm condition or after a certain number of alarm conditions or a certain amount of time spent in an alarm condition.

In addition to monitoring the provision of plasma to the adsorption device 170, the controller of the centrifuge system 10 also monitor the location of the interface 150, as described above. Slowing the plasma flow rate may be necessary to avoid overloading the adsorption device 170, but it also may tend to move the interface 150 away from the ideal location on the ramp 152. Accordingly, if the demands of the adsorption device 170 would slow the plasma flow to the point that it interferes with the maintenance of the interface 150 at a suitable location, operation of the system may be adjusted such that plasma is removed from the blood separation chamber 34 at a greater rate than the rate at which the plasma is flowed into the adsorption device 170. In such a case, the excess plasma (on account of the difference in flow rates out of the blood separation chamber 34 and into the adsorption device 170) may be routed to a different location (e.g., a storage container) for later processing by the adsorption device 170 or as a waste product or returned to the blood source without being processed by the adsorption device 170. Such a situation can typically be avoided by proper selection of an adsorption device 170 to be used with the blood separation system, though the composition of the blood will affect the plasma flow rate required to maintain the interface 150 at the ideal location, so it may be advantageous to program the controller such that it will be prepared to respond to such a situation. This is also applicable to the active blood treatment system and the adsorption device 172 employed therein.

The separation and reinfusion process when combining the blood separation system and adsorption device 170 may be substantially the same as the separation and reinfusion process when the blood separation system is used alone. However, it may be advantageous for the controller of the centrifuge system 10 to be programmed to perform a different blood separation process, depending on whether or not an adsorption device 170 is connected to the system. For example, it may be advantageous for the reinfusion step to be different when an adsorption device 170 is employed. Typically, the flow circuit 12 is flushed with fluid (e.g., saline) following separation to return any cellular components in the system to the blood source. When an adsorption device 170 is employed, it may be preferred to direct any flushed cellular components from the blood separation chamber 34 to the blood source along a path which bypasses the adsorption device 170. It is desirable to avoid flowing cellular components through the adsorption device 170 because they could clog or damage the adsorption device 170. The adsorption device 170 may be bypassed by proper programming of the valve actuators 134 of the cassette holder 94. Similar steps may also be taken during a separation procedure in the event of the separated plasma becoming contaminated with cellular components prior to entering the adsorption device 170. In particular, if the controller determines that the plasma has been contaminated, the plasma may be routed around the adsorption device 170 to avoid damage to the device. This is also applicable to the active blood treatment system and the adsorption device 172 employed therein.

2. Active Blood Treatment System

The flow circuit 12 and adsorption device 172 of an active blood treatment system are illustrated in FIG. 17. Besides the inclusion of the adsorption device 172, the flow circuit 12 of FIG. 17 is substantially identical to the one of FIG. 2, except that it includes an additional container or reservoir 184 associated with the center cassette 16a. In the embodiment of FIG. 17, the reservoir 184 is shown as being connected to tubing 185 leading to the top of the center cassette 16a, but the reservoir 184 may be otherwise connected to the middle cassette 16a. For example, the reservoir 184 may instead be connected to tubing 187 which extends from the bottom of the middle cassette 16a. The container 184 may be a flexible fluid container according to known design and is configured to receive and dispense processed plasma, as will be described in greater detail herein.

The adsorption device 172 is provided with connectors 186 which are suitable for fluidly associating the adsorption device 172 with the flow circuit 12. In the illustrated embodiment, the connectors 186 comprise sharpened cannulae, which are suitable for piercing flexible containers or reservoirs 44 and 184 or access ports thereof. Depending on the manner in which the adsorption device 172 is to be fluidly connected to the flow circuit 12, different connectors may also be employed without departing from the scope of the present disclosure.

In contrast to the adsorption device 170 of FIG. 16, the adsorption device 172 of FIG. 17 includes more than an adsorption column. In the illustrated embodiment, the adsorption device 172 of FIG. 17 includes a component 174 for removing undesirable substances from plasma (typically provided as an adsorption column), a fluid flow element 176 (such as a pump) for flowing plasma through the adsorption column 174, and a controller 178 for controlling the operation of the fluid flow element 176 and other aspects of the performance of the adsorption device 172. The controller 178 may be variously provided, but is typically provided as a computer which monitors the various components of the adsorption device 172. One example of a known controller is the Citem 10 monitor, which is employed with or as a part of the Immunosorba™ adsorption device from Fresenius Medical Care Deutschland GmbH.

FIG. 17 illustrates an adsorption device 172 with one fluid flow element 176 and one adsorption column 174, but it is possible to provide an adsorption device with a plurality of fluid flow elements and a plurality of adsorption columns. If multiple fluid flow elements and adsorption columns are employed, each adsorption column may include an associated fluid flow element or pump. The controller of the adsorption device may switch between the column-pump pairs, with one pair operating while another pair regenerates in preparation for operating again.

The fluid flow element 176 of the adsorption device 172 operates independently of the controller of the centrifuge system 10, so other provisions are made to give the controller some awareness of the operation of the fluid flow element 176 of the adsorption device 172. This may be achieved in a number of ways, but in a preferred embodiment, separated plasma is flowed into a location by the pump(s) 92 of the centrifuge system 10 and then the plasma is flowed from the location into the adsorption device 172 by the fluid flow element 176 of the adsorption device 172. A similar arrangement may be employed at the outlet of the adsorption device 172 (i.e., with the fluid flow element 176 of the adsorption device 172 flowing processed plasma to a location and then the pump(s) 92 of the centrifuge system 10 flowing plasma away from the location). The controller of the centrifuge system 10 monitors the characteristics of the locations(s) to ascertain the rate of the fluid flow element 176, which may be used to control the operation of the pump(s) 92 of the centrifuge system 10.

In the illustrated embodiment, the aforementioned locations are flexible containers or reservoirs 44 and 184 of the flow circuit 12. More particularly, as shown in FIG. 17, an inlet into the adsorption column 174 is fluidly associated with one of the containers or reservoirs 44 of the flow circuit 12, while an outlet of the adsorption column 174 is fluidly associated with another container or reservoir 184 of the flow circuit 12. In the illustrated embodiment, each reservoir 44 and 184 is associated with a weight scale or sensor, which measures the weight of fluid in the reservoir. The weight scales are electrically coupled to the controller of the centrifuge system 10, and the controller uses the volume of fluid in one or both of the reservoirs 44 and 184 (as may be determined using the weight of the reservoirs 44 and 184) as a processing parameter, as will be described in greater detail herein. In the illustrated embodiment, the centrifuge system 10 includes a plurality of hooks or hangers 188 (FIG. 1) from which the reservoirs 44 and 184 may be hung. Each hanger 188 may include an associated weight scale in accordance with the above description. Other means for measuring the weight of the reservoirs 44 and 188 (e.g., by laying the reservoirs on a horizontal platform with an associated weight scale) may also be employed without departing from the scope of the present disclosure. Further, rather than measuring the weight of the reservoirs 44 and 184, other means for determining the amount or volume of fluid therein (e.g., using an optical sensor to detect the fluid level) may also be employed.

In a separation procedure, plasma is separated from anticoagulated whole blood and pumped from the blood separation chamber 34 into the right cassette 16b by one or more pumps 92 of the centrifuge system 10. The plasma pump(s) of the centrifuge system 10 then flows the plasma through the right cassette 16b, through tubing 46, and into the pre-adsorption reservoir 44. In the embodiment of FIG. 17, the lower pump 92 associated with the right cassette 16b serves as the sole plasma pump, but other pumping arrangements may also be employed without departing from the scope of the present disclosure.

The fluid flow element 176 of the adsorption device 172 draws plasma from the pre-adsorption reservoir 44 and through the adsorption device 172. The adsorption column 174 of the adsorption device 172 receives the separated plasma from the blood separation system and processes it to remove undesirable substances by adsorption. The processed plasma flows out of the adsorption column 174 and back into the flow circuit 12 of the blood separation system, where it enters the post-adsorption reservoir 184. The processed plasma may then be returned to the blood source from the post-adsorption reservoir 184 by operation of one or more return or RF ("return fluid") pumps of the centrifuge system 10. In the embodiment of FIG. 17, the lower pump 92 associated with the middle cassette 16a serves as the sole RF pump, but other pumping arrangements may also be employed without departing from the scope of the present disclosure.

As with a passive blood treatment system, a blood separation procedure employing an active blood treatment system may either proceed generally according to conventional design or may include special provisions (e.g., routing any flushed cellular components around the adsorption device 172 during the reinfusion stage or in the event of plasma contamination).

As outlined above, a given adsorption device will be capable of processing only a certain amount of fluid, above which amount the adsorption device may become clogged or non-functional. Similar to the above-described passive blood treatment system, when practicing an active blood treatment system, the controller of the centrifuge system 10 may take as inputs or processing parameters one or more characteristics of the flow of plasma into the adsorption device 172. However, in an active system, the operation of the fluid flow element 176 (which functions independently of the controller of the centrifuge system 10) determines the rate and pressure of plasma flowing into and through the adsorption column 174. In an active system, the controller of the centrifuge system 10 may have other responsibilities, including acting as a safety mechanism, as it is able to calculate the amount of blood outside of the body and being processed and take steps to prevent a dangerously low ECV.

a. Inlet Flow Monitoring

The volume of fluid in the pre-adsorption reservoir 44 is monitored to ensure that, once it reaches an appropriate level and the fluid flow element 176 begins drawing plasma into the adsorption device 172, the volume remains stable (within an allowable range). A variety of indicators may be used to ascertain the volume of fluid in the pre-adsorption reservoir 44. In a preferred embodiment which will be described in greater detail herein, the weight of the reservoir 44 is monitored to determine the volume of fluid, but other factors (e.g., the number of strokes performed by the fluid flow element which flows fluid into the reservoir 44) may also be considered in monitoring the volume of fluid in the reservoir 44.

When the weight of the pre-adsorption reservoir 44 is maintained at least generally or substantially stable during the adsorption stage, the amount of plasma flowing into the pre-adsorption reservoir 44 (due to the operation of the plasma pump(s) of the centrifuge system 10) will be at least generally or substantially the same as the amount of plasma flowing out of the pre-adsorption reservoir 44 and into the adsorption device 172 (due to operation of the fluid flow element 176). On the other hand, if the weight of the pre-adsorption reservoir 44 is outside of the target range, it is indicative of improper fluid flow and exchange from the flow circuit 12 to the adsorption device 172, in which case the controller of the centrifuge system 10 will correct the operation of the plasma pump(s) to stabilize the weight of the pre-adsorption reservoir 44. In some circumstances, the controller may also instruct a technician to adjust the operation of the adsorption device 172, as will be described in greater detail below. An exemplary control scheme for monitoring the weight of the pre-adsorption reservoir 44 (and, hence, the flow rate of plasma entering the adsorption device 172) is illustrated in FIG. 18.

Prior to separated plasma entering the pre-adsorption reservoir 44, the reservoir 44 will be at least partially filled with the saline used to prime the flow circuit 12. Thus, the first fluid drawn into the adsorption device 172 will be saline. Initially, the plasma pump(s) of the centrifuge system 10 will be programmed to operate at a plasma pump flow rate Qp (illustrated in FIG. 18 as the top rectangle). The plasma pump flow rate Qp is equal to a determined maximum safe flow rate multiplied by an adjustment factor Qp_Adj. The determined maximum safe flow rate will vary from system to system but, in the illustrated embodiment, the determined maximum safe flow rate will be equal to the smallest of a number of possible limiting rates. These possible rates include the flow rate of whole blood into the blood separation chamber 34, the flow rate of plasma exiting the blood separation chamber 34 which maintains the interface 150 at the proper location on the ramp 152 (FIG. 10), and the maximum allowable flow rate of fluid entering the adsorption device 172. The adjustment factor is a variable no greater than 1 which determines the percentage of the determined maximum safe flow rate at which the plasma pump(s) will actually operate. If conditions are such that the plasma pump(s) may be safely operated at the determined maximum safe flow rate, then the adjustment factor will be set to 1. If conditions are such that the plasma pump(s) should be deactivated, then the adjustment factor will be set to 0. If conditions are such that it is desirable for the plasma pump(s) to operate at a slower rate, then the adjustment factor may be set to a number between 0 and 1. The various conditions for setting the adjustment factor to different values will be described in greater detail herein.

As saline is removed from the pre-adsorption reservoir 44 by the fluid flow element 176 of the adsorption device 172, separated plasma will begin flowing into the pre-adsorption reservoir 44. Depending on the relative rates of the pumps 92 and 176 of the centrifuge system 10 and the adsorption device 172, the weight of the pre-adsorption reservoir 44 (identified in FIG. 18 as "Wp") may increase or decrease. Initially, it may be advantageous for the weight of the pre-adsorption reservoir 44 to increase to ensure a suitable supply of plasma to the adsorption device 172. This may be referred to as the "build-up" stage.

Figure 18:
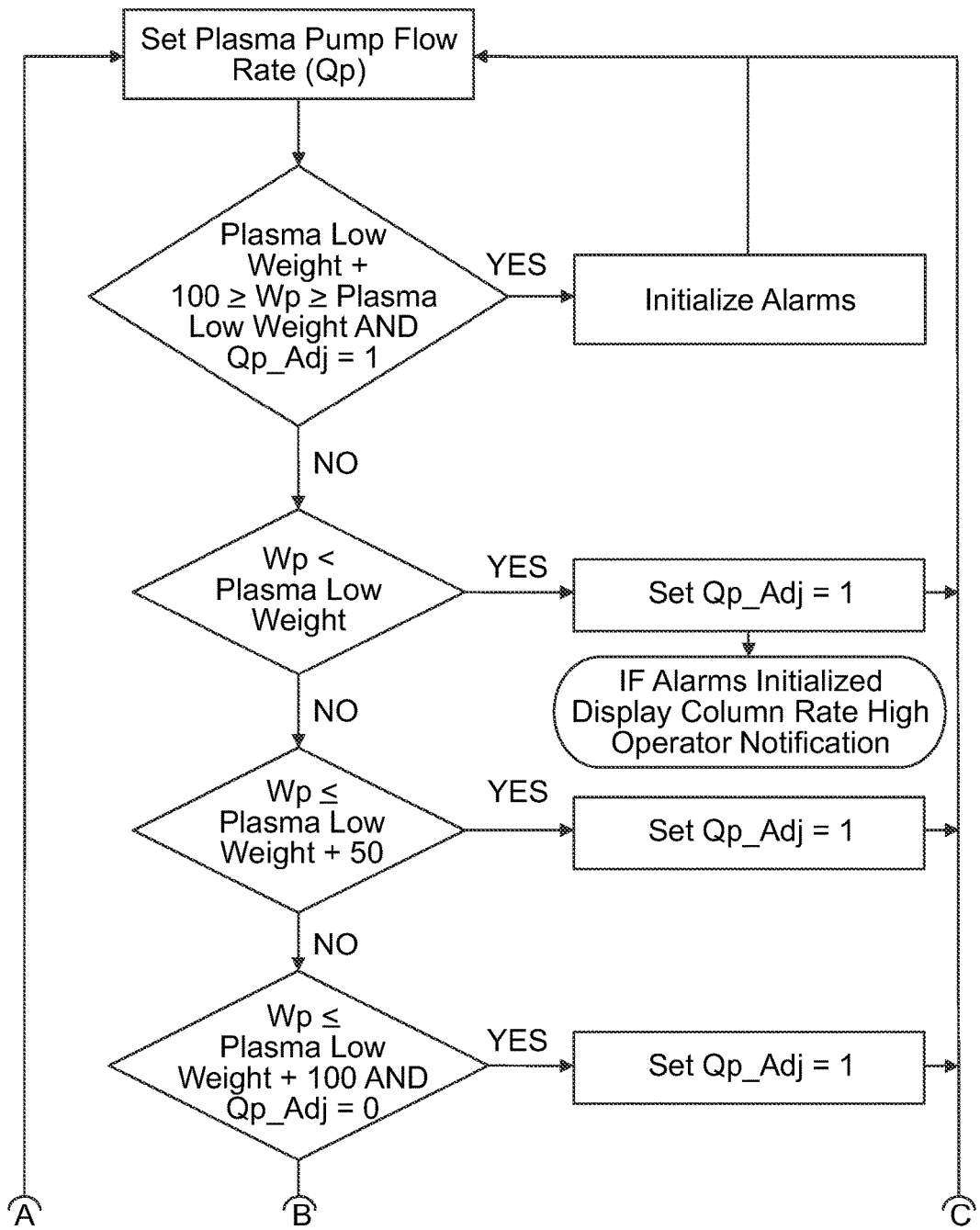
FIG. 18 is a flowchart which shows programming of a controller for controlling the rate of fluid flow into the adsorption device of FIG. 17.
Figure 18:
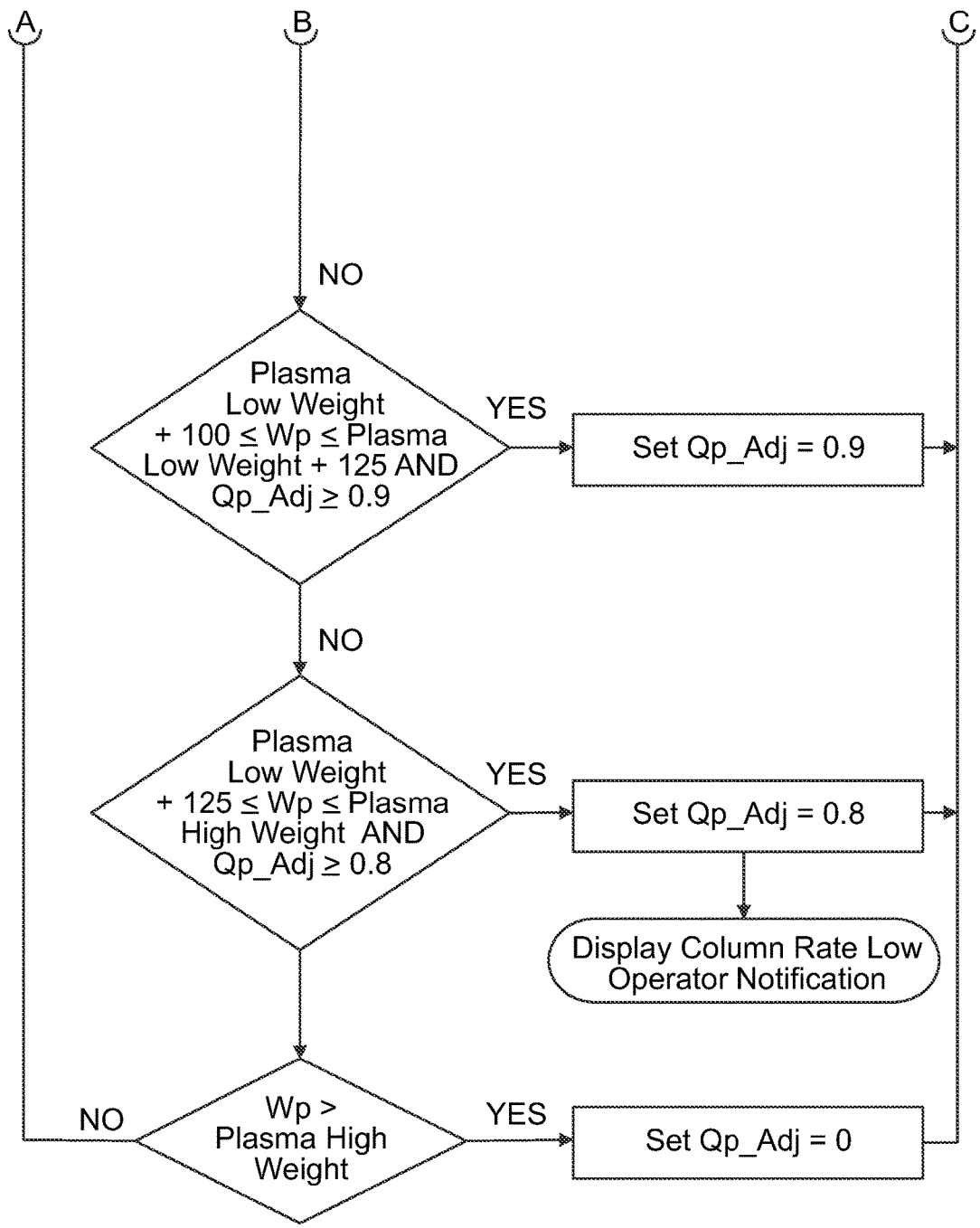

During the "build-up" stage (and whenever the controller of the centrifuge system 10 has set or reset the plasma pump flow rate), the controller checks whether the weight of the pre-adsorption reservoir 44 is within a predetermined range, as represented by the top diamond of FIG. 18. Any target range may be employed without departing from the scope of the present disclosure but, in the illustrated embodiment, the target range is from a predetermined minimum weight of the reservoir 44 ("Plasma Low Weight") to an upper limit which is 100 grams greater than the Plasma Low Weight.

If the weight of the reservoir 44 is outside of the target range (i.e., when the answer to the query of the top diamond of FIG. 18 is "NO"), it is an indication that there is either too much or too little fluid in the pre-adsorption reservoir 44 for the preferred processing conditions. The controller of the centrifuge system 10 will then perform a number of other checks (represented by the other diamonds of FIG. 18) to determine the proper response which will move the weight of the reservoir 44 into the target range. During the "build-up" stage, there should not be too much fluid in the pre-adsorption reservoir 44, so the controller of the centrifuge system 10 effectively checks (in the weight check represented by the top diamond of FIG. 18) whether a sufficient amount of plasma has been allowed to build up in the reservoir 44.

If the controller determines that the weight of the pre-adsorption reservoir 44 is outside of the target range, it will first check whether the weight is less than Plasma Low Weight. This step is represented in FIG. 18 by the second diamond. If the weight is less than Plasma Low Weight (i.e., when the answer to the query of the second diamond is "YES"), the controller will set the adjustment factor to 1 and return to the "Set Plasma Pump Flow Rate (Op)" step. With the adjustment factor set to 1, the plasma pump(s) of the centrifuge system 10 will operate at 100% of the aforementioned determined maximum safe flow rate, thereby tending to increase the amount of plasma in the pre-adsorption reservoir 44. The controller also checks whether the alarm states have been initialized, as will be described in greater detail below. During the "build-up" stage, the alarms will not have been initialized, so a low weight will not be treated as an error and the control process will start anew without activating an alarm.

The two weight checks represented by the top two diamonds of FIG. 18 will repeat until the weight of the pre-adsorption reservoir 44 falls within the target range (i.e., exceeds Plasma Low Weight). When the weight falls within the target range (i.e., when the answer to the query of the top diamond is "YES"), the alarm states will be initialized and the controller may continue periodically performing the first weight check (the top diamond of FIG. 18) as long as the weight of the pre-adsorption reservoir 44 remains within the target range and the adjustment factor remains set to 1.

If the weight of the pre-adsorption reservoir 44 again moves out of the target range or if the adjustment factor is set to a value different than 1 (i.e., when the answer to the query of the top diamond is "NO"), the controller of the centrifuge system 10 will proceed to check whether the weight is less than Plasma Low Weight, as represented by the second diamond of FIG. 18 and as described above. If the alarm states have been initialized and the controller determines that the weight of the reservoir 44 is less than Plasma Low Weight, it is an indication that the fluid flow element 176 of the adsorption device 172 is drawing fluid from the reservoir 44 at a rate which is too high for the plasma pump(s) of the centrifuge system 10 to safely match. The controller of the centrifuge system 10 cannot control the operation of the adsorption device 172, so it may instead display a "Column Rate High" operator notification, which instructs the operator to decrease the flow rate of the fluid flow element 176 of the adsorption device 172. In addition to triggering an alarm, the controller also sets the adjustment factor to 1, which causes the plasma pump(s) of the centrifuge system 10 to operate at 100% of the aforementioned determined maximum safe flow rate, thereby supplying plasma to the reservoir 44 as fast as allowable and tending to increase the amount of plasma in the pre-adsorption reservoir 44. Following the alarm and subsequent response thereto (or while a response is being performed by an operator), the control process may repeat itself and periodically trigger "Column Rate High" alarms until the weight of the reservoir 44 is back within the target range.

If, following the first and second weight check (the top and second diamonds of FIG. 18), the controller of the centrifuge system 10 determines that the weight of the reservoir 44 is not less than Plasma Low Weight (i.e., when the answer to the query of the second diamond is "NO"), it is an indication that the weight of the reservoir 44 is greater than the upper end of the target range and/or the adjustment factor is not set to 1. To determine which of these conditions is present, the controller may first check whether the weight of the reservoir 44 falls within a predetermined lower sub-range of the target range. This step is represented as the third diamond in FIG. 18. In the illustrated embodiment, the controller checks whether the weight of the reservoir 44 is within the bottom half of the target range (i.e., whether the weight of the reservoir 44 is no more than 50 grams more than Plasma Low Weight). If the controller determines that the weight of the reservoir 44 is within this lower sub-range (i.e., when the answer to the query of the third diamond is "YES"), it is an indication that the adjustment factor is set to a value less than 1 and that the plasma pump(s) of the centrifuge system 10 are flowing plasma into the pre-adsorption reservoir 44 at a rate less than the aforementioned highest safe plasma flow rate. Because the weight of the reservoir 44 is on the lower end of the target range, additional plasma may be flowed into the reservoir 44 without undue risk of exceeding the upper end of the target weight range. Accordingly, the controller may set the adjustment factor to 1 (thereby increasing the rate of the plasma pump(s) and tending to increase the weight of the reservoir 44) and return to the beginning of the control loop.

If the controller determines that the weight of the reservoir 44 does not fall within the aforementioned lower sub-range (i.e., when the answer to the query of the third diamond of FIG. 18 is "NO"), the controller proceeds to determine whether the weight falls within the target range and the adjustment factor is 0 (i.e., no plasma is being flowed into the reservoir 44). This step is represented by the fourth diamond of FIG. 18. As will be described in greater detail below, the adjustment factor will only be set to 0 if the weight of the reservoir 44 exceeds a predetermined maximum weight ("Plasma High Weight"). Stopping plasma flow into the reservoir 44 will cause the weight of the reservoir 44 to decrease, because the fluid flow element 176 of the adsorption device 172 continues to draw plasma out of the reservoir 44. When the plasma pump(s) of the centrifuge system 10 have been inactive for a suitable amount of time, the weight of the reservoir 44 will return to the target range and the answer to the query of the fourth diamond will be "YES." At this time, with the weight back in the target range again, the controller resets the adjust factor to a greater value (e.g., to a value of 1 in the illustrated embodiment), thereby causing the plasma pump(s) to again flow plasma into the reservoir 44.

If, during the fourth weight check (the fourth diamond of FIG. 18), the controller instead determines that the weight of the reservoir 44 does not fall within the target range and/or the adjustment factor is not set to zero (i.e., when the answer to the query of the fourth diamond of FIG. 18 is "NO"), the controller proceeds to determine whether the weight is within an allowable margin above the upper limit of the target range and the adjustment factor is greater than or equal to a particular reduced value. This step is represented by the fifth diamond of FIG. 18. In the illustrated embodiment, the allowable margin is 25 grams greater than the upper limit of the target range (i.e., a total of 125 grams above Plasma Low Weight) and the particular reduced value of the adjustment factor is 0.9, although a different margin and adjustment factor may also be employed without departing from the scope of the present disclosure. When these conditions are met (i.e., when the answer to the query of the fifth diamond is "YES"), it means that the weight of the reservoir 44 is only slightly above the upper end of the target range, so it is acceptable for the plasma pump(s) to operate at a slightly reduced rate. The controller of the centrifuge system 10, therefore responds by setting the adjustment factor to the particular reduced value (0.9 in the illustrated embodiment), which causes the weight of the reservoir 44 to either increase at a slower rate or decrease, depending on the rate of the fluid flow element 176 of the adsorption device 172.

If, during the fifth weight check (the fifth diamond of FIG. 18) the controller finds that the weight of the reservoir 44 is not within the allowable margin and/or the adjustment factor is not greater than or equal to the particular reduced value (i.e., when the answer to the query of the fifth diamond is "NO"), the controller proceeds to determine whether the weight is less than Plasma High Weight and the adjustment factor is greater than or equal to a particular further reduced value. This step is represented by the sixth diamond of FIG. 18. The further reduced value is less than the aforementioned reduced value and, in the illustrated embodiment, the particular further reduced value of the adjustment factor is 0.8, although a different adjustment factor may also be employed without departing from the scope of the present disclosure. When these conditions are met (i.e., when the answer to the query of the sixth diamond is "YES"), it means that the weight of the reservoir 44 is greater than the aforementioned allowable margin and approaching the maximum allowable weight so, while it is still acceptable for the plasma pump(s) to operate, it is preferable for it to operate at a further reduced rate. The controller of the centrifuge system 10, therefore responds by setting the adjustment factor to the particular further reduced value (0.8 in the illustrated embodiment), which causes the weight of the reservoir 44 to either increase at a slower rate or decrease, depending on the rate of the fluid flow element 176 of the adsorption device 172.

In addition to setting the adjustment factor to the further reduced value, the controller may also display a "Column Rate Low" operator notification, which instructs the operator to increase the flow rate of the fluid flow element 176 of the adsorption device 172 (if doing so would not increase the rate above the maximum rate which can be accommodated by the adsorption device 172). Following the alarm and subsequent response thereto (or while a response is being performed by an operator), the control process may repeat itself and periodically trigger "Column Rate Low" alarms until the weight of the reservoir 44 is back within the target range.

If, after performing the weight check represented by the sixth diamond of FIG. 18, the controller of the centrifuge system 44 registers with a "NO" response to the query, the controller moves on to a final check, which is represented by the bottom diamond of FIG. 18. In the final check, the controller compares the weight of the reservoir 44 to Plasma High Weight. If the weight is less than Plasma High Weight (i.e., when the answer to the query of the bottom diamond is "NO"), the control process will restart without making any adjustments to the plasma pump rate or triggering any alarms. On the other hand, if the weight of the reservoir 44 is greater than the Plasma High Weight (i.e., when the answer to the query of the bottom diamond is "YES"), the controller will set the adjustment factor to 0, thereby deactivating the plasma pump(s) and preventing the weight of the reservoir 44 from getting any larger than the maximum allowable rate. With the plasma pump(s) deactivated, the continued operation of the fluid flow element 176 of the adsorption device 172 will cause the weight of the reservoir 44 to eventually decrease to an acceptable level, at which time the plasma pump(s) may be restarted. Maintaining the weight of the reservoir 44 below a given level is also advantageous as a safety mechanism, as excessive fluid in the reservoir 44 is indicative of a low ECV, which can be dangerous for the patient.

b. Outlet Flow Monitoring

As with the pre-adsorption reservoir 44, the volume of fluid in the post-adsorption reservoir 184 (which may be determined by a variety of means, including the preferred method of measuring the weight of the reservoir 184) may also be used as a processing parameter. The weight of the post-adsorption reservoir 184 is monitored to ensure that, once it reaches an appropriate level and the RF pump(s) of the centrifuge system 10 begin drawing plasma out of the reservoir 184, the weight remains stable (within an allowable range). When the weight of the post-adsorption reservoir 184 is maintained at least generally or substantially stable during the adsorption stage, the amount of plasma flowing out of the adsorption device 172 (due to the operation of the fluid flow element 176 of the adsorption device 172) will be at least generally or substantially the same as the amount of processed plasma pumped out of the flow circuit 12 and back to the blood source (due to operation of the RF pump(s) of the centrifuge system 10). On the other hand, if the weight of the post-adsorption reservoir 184 is outside of the target range, it is indicative of improper fluid flow and exchange from the adsorption device 172 to the flow circuit 12, in which case the controller of the centrifuge system 10 will correct the operation of the RF pump(s) to stabilize the weight of the post-adsorption reservoir 184. In some circumstances, the controller may also instruct a technician to adjust the operation of the adsorption device 172, as will be described in greater detail below. An exemplary control scheme for monitoring the weight of the post-adsorption reservoir 184 (and, hence, the flow rate of plasma exiting the adsorption device 172) is illustrated in FIG. 19.

Prior to saline or processed plasma entering the post-adsorption reservoir 184, the reservoir 184 will be substantially empty. As there is no fluid to draw from the reservoir 184, the RF pump(s) will initially be inactive. When the reservoir 184 reaches a threshold weight, the RF pump(s) may begin operating at a RF pump flow rate Qrf. The RF pump flow rate may be equal to any of a number of different values but, in the illustrated embodiment, the RF pump flow rate may be set to one of three levels. At a "Low Speed" setting, the RF pump(s) is deactivated and no fluid is drawn out of the post-adsorption reservoir 184. The "Low Speed" setting also prevents air from entering the flow circuit 12. The RF pump(s) is set to Low Speed (i.e., inactive) prior to the reservoir 184 reaching the aforementioned threshold weight. At a "Normal Speed" setting, the RF pump(s) operates at a rate equal to the plasma pump flow rate Qp, so that the rate of fluid entering the adsorption device 172 (Qp) will be substantially the same as the rate of fluid exiting the adsorption device 172 (Qrf). As will be described in greater detail below, the RF pump(s) is set to operate at Normal Speed when the weight of the reservoir 184 first reaches the aforementioned threshold weight. Finally, at a "High Speed" setting, the RF pump(s) operates at the highest rate possible without the totality of the return components (including the fluids flowed to the blood source without passing through the adsorption device 172) exceeding the predetermined citrate infusion rate, which is defined as the maximum rate at which the blood source can metabolize the anticoagulant which is returned thereto following separation of the whole blood. More particularly, in one embodiment, High Speed is equal to EqQb−Qwb+Qp, with EqQb representing the equivalent safe fluid return rate (which is based on various factors, such as citrate infusion rate, weight of the patient/donor (if the blood source is a human), anticoagulant ratio, and the type of anticoagulant being used) and Qwb representing the rate at which whole blood is drawn from the blood source into the flow circuit 12. The conditions under which the rate of the RF pump(s) is changed will be described in greater detail below.

Figure 19:
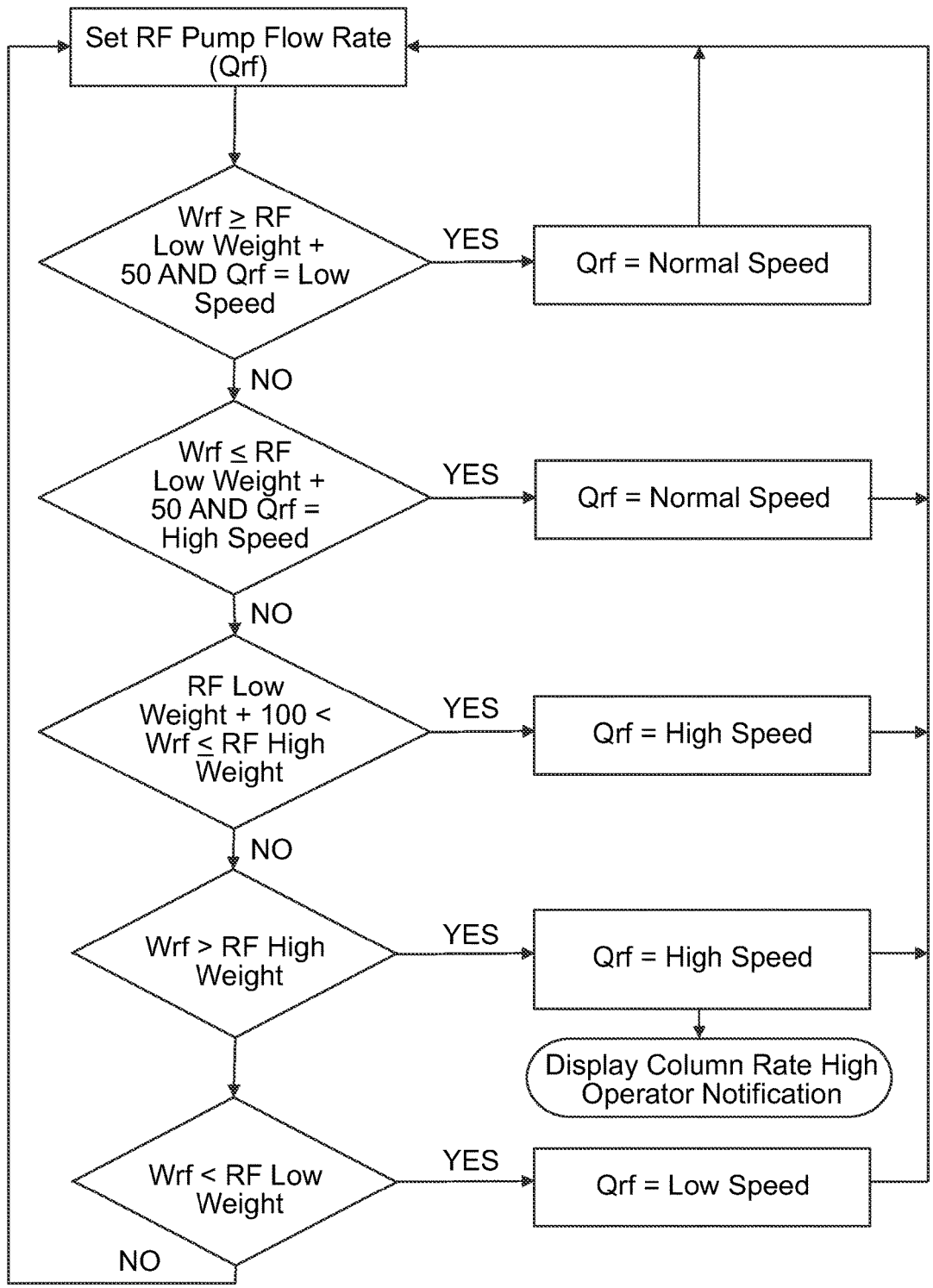
FIG. 19 is a flowchart which shows programming of a controller for controlling the rate of fluid flow out of the adsorption device of FIG. 17.

The step of checking to see whether the weight of the reservoir 184 (identified in FIG. 19 as "Wrf") has reached the threshold level is represented by the top diamond of FIG. 19. The threshold level may be any value but, in the illustrated embodiment, it is equal to an amount 50 ml greater than a predetermined minimum weight of the reservoir 184 and the return fluid therein ("RF Low Weight"). As saline and plasma are pumped through the adsorption device 172, the weight of the reservoir 184 will gradually increase.

While the weight is less than the threshold level and initially building up, the controller will continue through a number of weight checks (represented in FIG. 19 by the various diamonds) until it gets to a final weight check (the bottom diamond of FIG. 19), where the controller checks if the weight of the reservoir 184 is less than RF Low Weight. The controller confirms that the weight is still less than RF Low Weight (i.e., it responds to the query of the bottom diamond of FIG. 19 with a "YES"), so it maintains the RF pump flow rate at Low Speed and returns to the beginning of the control loop.

After cycling through the control loop a sufficient number of times, the weight of the reservoir 184 will eventually exceed the threshold level, at which time the controller will check (in the top diamond of FIG. 19) whether the RF pump(s) is operating at Low Speed. If the RF pump(s) is not operating at Low Speed (i.e., when the answer to the query of the top diamond is "NO"), the controller will continue through the other weight checks illustrated in FIG. 19. On the other hand if, as during the initial "build-up" stage, the RF pump(s) is operating at Low Speed (i.e., when the answer to the query of the top diamond is "YES"), it signals that the "build-up" stage has ended and it is safe to draw fluid out of the post-adsorption reservoir 184, so the controller proceeds to change the RF pump operation rate to Normal Speed. With the RF pump(s) operating at Normal Speed, the weight of the reservoir 184 will either increase at a slower rate or may begin to decrease, depending on the rate of the fluid flow element 176 of the adsorption device 172.

With the RF pump(s) operating at Normal Speed, the controller will return to the beginning of the control loop of FIG. 19 and respond to the first weight check (i.e., the top diamond) with a "NO" and advance to the second weight check (the second diamond). During the second weight check, the controller checks whether the weight of the reservoir 184 is less than the threshold level and the RF pump flow rate is set to High Speed. Operating the RF pump(s) at High Speed will tend to decrease the weight of the reservoir 184, so it should not be done when the weight is less than the threshold value because of the risk of the weight dropping below RF Low Weight. If the controller finds that such conditions exist (i.e., when the answer to the query of the second diamond is "YES"), it will set the RF pump flow rate to Normal Speed, which decreases the risk of the weight of the reservoir 184 dropping below RF Low Weight. If the controller finds that such conditions do not exist (i.e., when the answer to the query of the second diamond is "NO"), it will move to the next weight check.

In the next weight check (the third diamond of FIG. 19), the controller of the centrifuge system 10 checks whether the weight of the reservoir 184 is approaching a predetermined maximum weight ("RF High Weight"). In the illustrated embodiment, the controller does this by checking if the weight of the reservoir 184 is at least 100 ml greater than RF Low Weight, while still being less than RF High Weight. Other approaches to assessing the proximity of the weight of the reservoir 184 to a maximum value may also be employed without departing from the scope of the present disclosure. If the controller determines that the weight of the reservoir 184 is sufficiently close to RF High Weight (i.e., when the answer to the query of the third diamond is "YES"), the controller sets the RF pump flow rate to High Speed to attempt to decrease the weight of the reservoir 184. If the controller finds that the weight of the reservoir 184 is not sufficiently close to RF High Weight (i.e., when the answer to the query of the third diamond is "NO"), it will move to the next weight check.

In the next weight check (the fourth diamond of FIG. 19), the controller checks whether the weight of the reservoir 184 is greater than RF High Weight. If the controller finds the weight to be greater than RF High Weight (i.e., when the answer to the query of the fourth diamond is "YES"), it is an indication that the amount of fluid in the post-adsorption reservoir 184 is continuing to increase because the fluid flow element 176 of the adsorption device 172 is operating at a rate that cannot safely be matched by the RF pump(s) of the centrifuge system 10. The controller of the centrifuge system 10 cannot control the operation of the adsorption device 172, so it may instead display a "Column Rate High" operator notification, which instructs the operator to decrease the flow rate of the fluid flow element 176 of the adsorption device 172. In addition to triggering an alarm, the controller also sets (or maintains) the RF pump flow rate at High Speed, which attempts to decrease the amount of return fluid in the post-adsorption reservoir 184. Following the alarm and subsequent response thereto (or while a response is being performed by an operator), the control loop may repeat itself and periodically trigger "Column Rate High" alarms until the weight of the reservoir 184 is below RF High Weight.

Finally, if the controller of the centrifuge system 10 determines that the weight of the reservoir 184 is not greater than RF High Weight (i.e., when the answer to the query of the fourth diamond of FIG. 19 is "NO"), the controller will check if the weight is less than RF Low Weight (the bottom diamond of FIG. 19). If the controller finds the weight of the reservoir 184 to be less than RF Low Weight (i.e., when the answer to the query of the bottom diamond is "YES"), it will set the RF pump flow rate to Low Speed to deactivate the RF pump(s) and attempt to increase the weight of the reservoir 184. On the other hand, if the controller finds the weight of the reservoir 184 to be greater than RF Low Weight (i.e., when the answer to the query of the bottom diamond is "NO"), it will return to the beginning of the control loop of FIG. 19 without making any change to the RF pump flow rate or triggering any alarm.

In addition to the "Column Rate High" alarm shown in FIG. 19, the controller of the centrifuge system 10 may check other features and parameters of the blood treatment system and trigger other safety alarms if it finds anything wrong. For example, if conditions suggest that the post-adsorption reservoir 184 is not properly connected (e.g., if the reservoir 184 becomes detached during operation and the controller measures a zero weight or an unusually low weight), the controller may trigger a "Return Bag Removed" alarm. Similarly, the controller of the centrifuge system 10 may also monitor the weight of the reservoir 184 during the initial "build-up" stage and, if the weight does not increase, an alarm may be triggered to indicate that the reservoir 184 is not properly connected.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood treatment system comprising, in combination:
   a blood separation system configured to separate a blood component from blood; and
   a disposable flow circuit including
      a blood separation chamber in which the blood component is separated from the blood,
      an adsorption device that is separate from the blood separation system and configured to receive at least a portion of said blood component from the blood separation system,
      at least one cassette fluidly connected between the blood separation chamber and the adsorption device and including a plurality of valve stations configured to be actuated by the blood separation system to direct fluid flow through the at least one cassette, and
      a plurality of containers fluidly connected to the at least one cassette, wherein the blood separation system includes
      a fluid flow element configured to actuate the at least one cassette for flowing said at least a portion of said blood component from the blood separation system continuously into the adsorption device,
      a plurality of valve actuators each configured to alternately open and close an associated one of the plurality of valve stations to change fluid flow through the at least one cassette, and
      a controller configured to
         control the fluid flow element based at least in part on one or more processing parameters including a maximum flow rate of said at least a portion of said blood component flowed into the adsorption device and/or a maximum pressure of said at least a portion of said blood component flowed into the adsorption device, and
         actuate at least one of the plurality of valve actuators to change fluid flow through the at least one cassette so as to selectively allow and prevent fluid communication between the at least one cassette and at least one of the plurality of containers during flow of said blood component out of the blood separation system, with at least a portion of the blood component flowing out of the blood separation chamber being directed from the at least one cassette into said at least one of the plurality of containers instead of flowing from the at least one cassette into the adsorption device when there is fluid communication between the at least one cassette and said at least one of the plurality of containers, wherein
         allowing fluid communication between the at least one cassette and said at least one of the plurality of containers during flow of said blood component out of the blood separation system causes the blood component to be flowed out of the blood separation chamber at a flow rate that is different from an actual flow rate at which said at least a portion of said blood component is flowed into the adsorption device and/or at a pressure that is different from an actual pressure at which said at least a portion of said blood component is flowed into the adsorption device, and
         said actual flow rate is greater than zero.

2. The blood treatment system of claim 1, wherein the controller is configured to receive as input the maximum flow rate and/or the maximum pressure at which said at least a portion of said blood component is to be flowed into the adsorption device.

3. The blood treatment system of claim 1, wherein the controller is pre-programmed with the maximum flow rate and/or the maximum pressure at which said at least a portion of said blood component is to be flowed into the adsorption device.

4. The blood treatment system of claim 1, wherein the blood separation system further includes at least one pressure sensing transducer configured to cooperate with the controller to determine the actual pressure and/or actual flow rate at which said at least a portion of said blood component is being flowed into the adsorption device.

5. The blood treatment system of claim 1, wherein the blood separation system further includes at least one weight scale configured to cooperate with the controller to determine the actual flow rate at which said at least a portion of said blood component is being flowed into the adsorption device.

6. The blood treatment system of claim 1, wherein
   the blood separation system includes a centrifuge in which the blood component is separated from the blood, and
   the controller is configured to allow the blood component to be flowed out of the centrifuge at a greater flow rate than the actual flow rate at which said at least a portion of said blood component is flowed into the adsorption device.

7. The blood treatment system of claim 1, wherein the controller is configured to execute a reinfusion procedure following the blood separation system separating the blood component from blood and the adsorption device receiving said at least a portion of said blood component, the reinfusion procedure comprising flowing fluid to a blood source along a path that bypasses the adsorption device.

8. The blood treatment system of claim 1, wherein the controller is configured to determine whether said blood component separated from the blood includes a cellular blood component and, if so, to prevent said blood component from flowing into the adsorption device.

9. The blood treatment system of claim 1, wherein
   the flow circuit includes a tubing including an upstream portion and a downstream portion,
   the upstream portion of the tubing includes an upstream connector connected to an upstream portion of the adsorption device,
   the downstream portion of the tubing includes a downstream connector connected to a downstream portion of the adsorption device, and
   the upstream and downstream connectors are configured to be disconnected from the adsorption device and directly connected to each other.

10. The blood treatment system of claim 9, wherein one of the upstream and downstream connectors comprises a male part of a luer connector and the other one of the upstream and downstream connectors comprises a female part of the luer connector that mates with the male part of the luer connector.

11. The blood treatment system of claim 1, wherein
   the fluid flow element comprises a peristaltic pump, and
   the at least one cassette includes at least one tubing loop configured to cooperate with the peristaltic pump.

12. A blood treatment system comprising, in combination:
a blood separation system configured to separate a blood component from blood; and
a disposable flow circuit including
- a blood separation chamber in which the blood component is separated from the blood,
- an adsorption device that is separate from the blood separation system and configured to receive at least a portion of said blood component from the blood separation system,
- at least one cassette fluidly connected between the blood separation chamber and the adsorption device and including a plurality of valve stations configured to be actuated by the blood separation system to direct fluid flow through the at least one cassette, and
- a plurality of containers fluidly connected to the at least one cassette, including a vent container, wherein the blood separation system includes
- a fluid flow element configured to actuate the at least one cassette for flowing said at least a portion of said blood component from the blood separation system continuously into the adsorption device,
- a plurality of valve actuators each configured to alternately open and close an associated one of the plurality of valve stations to change fluid flow through the at least one cassette, and
- a controller configured to
  - control the fluid flow element based at least in part on one or more processing parameters including a maximum flow rate of said at least a portion of said blood component flowed into the adsorption device and/or a maximum pressure of said at least a portion of said blood component flowed into the adsorption device, and
  - actuate at least one of the plurality of valve actuators to change fluid flow through the at least one cassette so as to selectively allow and prevent fluid communication between the at least one cassette and the vent container during flow of said blood component out of the blood separation system to control an actual pressure at which said at least a portion of said blood component is flowed into the adsorption device, wherein
    - allowing fluid communication between the at least one cassette and the vent container during flow of said blood component out of the blood separation system causes the blood component to be flowed out of the blood separation chamber at a flow rate that is different from an actual flow rate at which said at least a portion of said blood component is flowed into the adsorption device and/or at a pressure that is different from the actual pressure at which said at least a portion of said blood component is flowed into the adsorption device, and
    - said actual flow rate is greater than zero.

\* \* \* \* \*